United States Patent [19]

Greenberg et al.

[11] Patent Number: 4,906,634

[45] Date of Patent: Mar. 6, 1990

[54] NOVEL N-[4-(AMINOSUBSTITUTED)PHENYL]METHANESULFONAMIDES AND THEIR USE AS CARDIOVASCULAR AGENTS

[75] Inventors: Stanley S. Greenberg, Morris Plains, N.J.; William C. Lumma, Jr., Pennsburg, Pa.; Klaus Nickisch, Berlin, Fed. Rep. of Germany; Ronald A. Wohl, Morris Plains, N.J.

[73] Assignee: Schering A.G., Berlin, Fed. Rep. of Germany

[21] Appl. No.: 165,315

[22] Filed: Mar. 8, 1988

[51] Int. Cl.⁴ .............. C07D 295/08; C07D 295/10; C07D 241/12; A61K 31/495; A61K 31/445

[52] U.S. Cl. .................... 514/255; 546/190; 546/208; 546/229; 546/235; 546/236; 548/556; 548/569; 548/570; 548/575; 564/99; 514/210; 514/212; 514/218; 514/238.2; 514/252; 514/326; 514/331; 514/408; 514/428; 514/605; 540/575; 540/609; 540/610; 544/159; 544/160; 544/165; 544/173; 544/388; 544/392; 544/395; 544/398; 544/402

[58] Field of Search ............. 564/80, 83, 85, 86, 564/89, 91, 99; 514/603, 604, 605, 210, 212, 218, 238.2, 252, 255, 331, 326, 408, 428; 540/609, 610, 575; 544/159, 160, 165, 173, 388, 392, 395, 398, 402; 546/229, 236, 235, 190, 208; 548/556, 569, 570, 575

[56] References Cited

U.S. PATENT DOCUMENTS

| | | | |
|---|---|---|---|
| 3,701,777 | 10/1972 | Edenhofer et al. | 514/255 |
| 3,833,576 | 9/1974 | Edenhofer et al. | 546/267 |
| 4,083,992 | 4/1978 | Smith | 514/603 |
| 4,137,328 | 1/1979 | Cox et al. | 514/620 |
| 4,404,224 | 9/1983 | Asato | 514/605 |
| 4,544,654 | 10/1985 | Davey et al. | 514/212 |
| 4,587,360 | 5/1986 | Buzby, Jr. | 514/604 |
| 4,596,827 | 6/1986 | Molloy et al. | 514/605 |
| 4,629,739 | 12/1986 | Davey et al. | 514/605 |
| 4,636,511 | 1/1987 | Ostermayer et al. | 514/311 |

FOREIGN PATENT DOCUMENTS

| | | |
|---|---|---|
| 244115 | 11/1987 | European Pat. Off. . |
| 245997 | 11/1987 | European Pat. Off. . |
| 2803688 | 8/1978 | Fed. Rep. of Germany ...... 514/603 |
| 2056968 | 3/1981 | United Kingdom . |

OTHER PUBLICATIONS

Cox et al, CA 77-34126a (1972), "β-α substituted 1-phenyl-2-(alkylamino)-alkanes, . . . ".

Garvey et al, CA 86-165073q (1977), "Adreneipic agents, 4, . . . ".

Lambelin et al, CA 87-117766s (1977), "Heterocyclic aminoalcohol derivatives".

Oshiro et al, CA 88-50671g (1978), "3,4-dihydrocarbostyril derivatives".

Continental Pharma, CA 90-22815e (1979), "Heterocyclic aminoalcohol".

Smith et al, CA 93-61023b (1980), "The Chemistry of Beta-Adrenergic Blocking Agents . . . ".

Oshiro et al, CA 100-191710x (1984), "Syntheses of 8-acylamino-3,4-dihydrocarbostyril . . . ".

Kabbe et al, CA 104-207157t (1986), "Substituted Benzopyrans and Their Medical Use".

Primary Examiner—Mukund J. Shah
Assistant Examiner—Cecilia Shen
Attorney, Agent, or Firm—Elizabeth A. Bellamy; John L. White; I. William Millen

[57] ABSTRACT

Novel N-[4-(aminosubstituted)phenyl]methanesulfonamides and their use as cardiovascular agents, especially as antiarrhythmic agents are described. Pharmaceutical formulations containing such compounds are also discussed.

26 Claims, No Drawings

NOVEL N-[4-(AMINOSUBSTITUTED)PHENYL]METHANESULFONAMIDES AND THEIR USE AS CARDIOVASCULAR AGENTS

FIELD OF THE INVENTION

This invention relates to novel substituted phenylmethanesulfonamides and their use as cardiovascular agents. More especially this invention describes novel N-[4-(aminosubstituted)phenyl]methanesulfonamides, their pharmaceutically acceptable salts and the pharmaceutical compositions containing them as active ingredients. It also relates to the method of using these compounds primarily in the treatment of arrhythmias, especially in the treatment of arrhythmias for which Class III agents are 15 effective. Some of the compounds are also useful as inotropic agents, vasodilator agents and β-blocking agents.

GENERAL DESCRIPTION OF THE INVENTION

Composition-of-Matter Aspect

In its composition-of-matter aspect this invention relates to novel N-[4-(aminosubstituted)phenyl]methanesulfonamides and their pharmaceutically acceptable salts. Particularly, this invention relates to the novel compounds defined by the following Formula I:

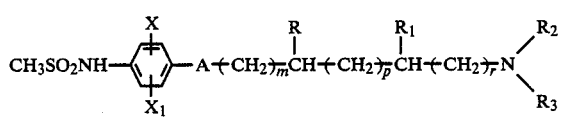

wherein
A is —O—, —S—, —SO, —SO$_2$— or

and m,p and r are the integers 0, 1 or 2.

R is hydrogen, methyl, ethyl or collectively with R$_1$ is a bond or an alkylene chain to form a saturated carbocyclic ring of from 3 to 6 ring atoms, or collectively with R$_2$ is a bond or alkylene chain to form a saturated monoheterocyclic ring of 5 to 6 ring atoms.

R$_1$ is hydrogen, methyl, ethyl or lower alkoxyloweralkyl.

R$_2$ is a C$_1$–C$_8$ straight or branched chain alkyl, allyl, optionally substituted phenylloweralkyl, cycloalkyl, cycloalkylloweralkyl or together with R$_3$ is an alkylene chain to form a heterocyclic ring of from 4 to 7 ring atoms or together with R$_3$ forms the system —CH$_2$-CH—O—CH$_2$—CH$_2$— or

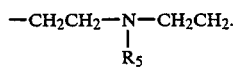

R$_3$ C$_1$–C$_8$ straight or branched chain alkyl, allyl, optionally substituted phenylloweralkyl, cycloalkyl or cycloalkylloweralkyl.

R$_4$ is hydrogen, C$_1$–C$_8$ straight or branched chain alkyl, allyl, optionally substituted phenylloweralkyl, cycloalkylloweralkyl or together with R$_2$ is an alkylene chain to form a saturated diheterocyclic ring of from 6 to 7 ring atoms.

R$_5$ is hydrogen or a C$_1$–C$_8$ straight or branched chain alkyl.

X, X$_1$ are the same or independently hydrogen, lower alkyl or one of X and X$_1$ is hydrogen and the other is in the ortho position to A and is the group

B is lower alkyl, phenyl, —CH=CH—D or —CH$_2$—CH$_2$—D.
D is

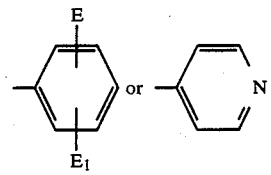

where E,E$_1$ are the same or independently hydrogen, lower alkyl, lower alkoxy or halogen.

The provisos in the foregoing are such that:
(a) when R and R$_1$ form a ring then R$_2$ together with R$_4$ cannot be a ring,
(b) the sum of m, p and r cannot be greater than 3,
(c) when one of X or X$_1$ is the group

then A must be —O—, and
(d) when A is —O—, —S—or

and either or both of R$_2$ an R$_3$ are optionally substituted phenylloweralkyl then the linkage between —A—and

cannot consist of a straight or branched chain alkyl.

Also contemplated as part of this invention are the pharmaceutically acceptable salts of the compounds of Formula 1. Useful acids for this purpose include inorganic acids such as hydrobromic, hydrochloric, sulfuric, phosphoric and organic acids such as acetic, propanoic, benzoic, naphthalenecarboxylic, oxalic, succinic, malic, maleic, adipic, lactic, tartaric, citric, salicyclic, methanesulfonic and p-toluenesulfonic.

It is to be understood that the definition of the compounds of Formula I encompasses all possible steroisomers and mixtures thereof, which possess the activity discussed below. In particular, it encompasses racemic modifications and any optical isomers which possess the indicated activity.

In the foregoing Formula I various terms are defined in the following manner. "Lower" alkyl/alkoxy shall refer to a straight or branched chain of from 1 to 4 carbon atoms, for example, methyl, ethyl, propyl, isopropyl, butyl, isobutyl, tertiary butyl and sec. butyl. The term $C_1$-$C_8$ straight or branched chain alkyl shall be inclusive but not limited to such moieties as methyl, ethyl, propyl, isopropyl, butyl, isobutyl, tertiary butyl, sec. butyl, pentyl, isopentyl, hexyl, 3-methylpentyl, heptyl, 2-methylhexyl, octyl and 2-ethylhexyl. The term cycloalkyl shall refer to a saturated carbocyclic ring containing 3 to 7 carbon atoms whilst cycloalkyl-loweralkyl shall refer to said cycloalkyl at the terminus of a 1–4 straight carbon chain. The term optionally substituted phenylloweralkyl shall refer to a phenyl group at the terminus of a $C_1$-$C_4$ straight carbon chain, said phenyl group being substituted by 1–3 substituents selected from hydrogen, chlorine, bromine, loweralkoxy, lower alkyl and trifluoromethyl. The term halogen shall refer to bromine, chlorine or fluorine. Preferred classes of compounds embodied by this invention are those of the above general Formula I having one of the following characteristics:

(a) A is —O—,
(b) A is —S—,
(c) A is -SO-,
(d) A is —$SO_2$—, or
(e) A is

The most preferred classes of compounds are those wherein A is —O— or

PROCESS ASPECT

In general, the compounds of this invention may be prepared using various processes and reactants known in the art. Scheme A-E are illustrative but not limiting of the methods and procedures for preparing the compounds of Formula I. The choice of any synthetic route is dependent on the substituents in Formula I and would be obvious to one skilled in the art.

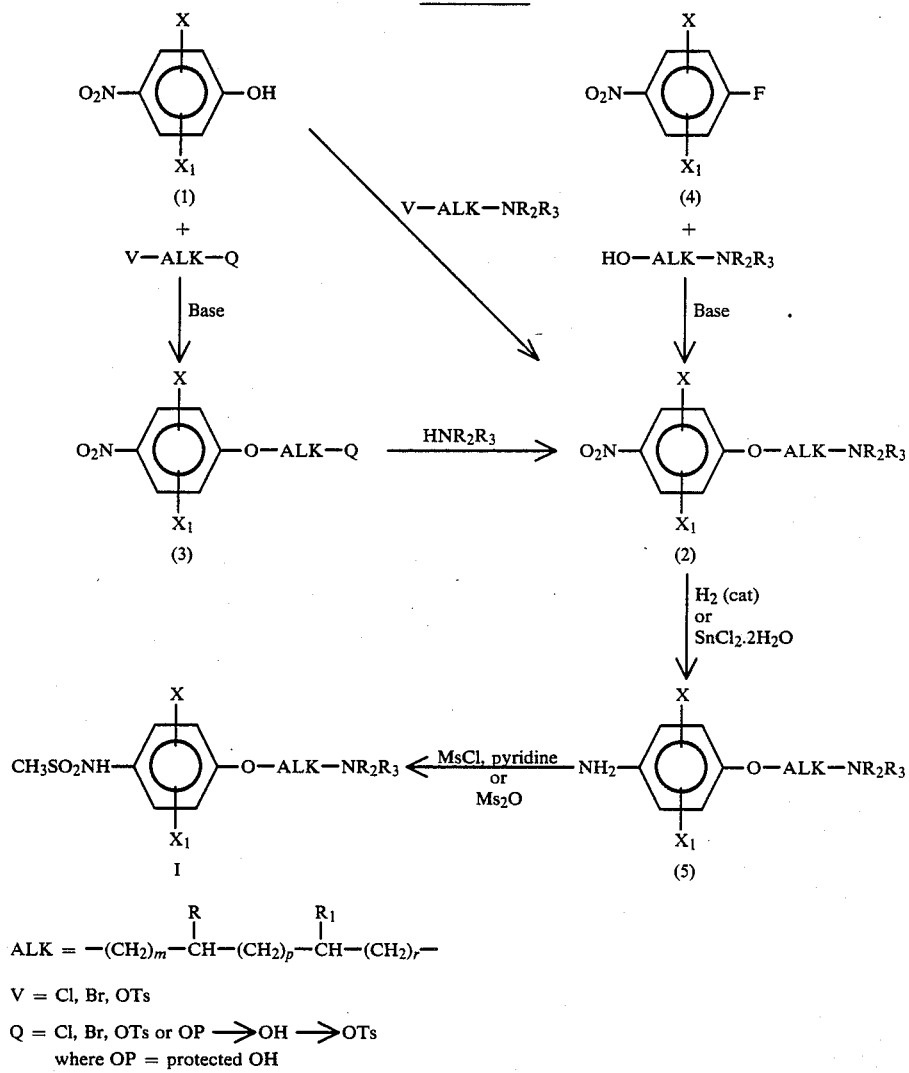

The foregoing Scheme A illustrates the methods for the preparation of the 4-methylsulfonamidophenyl ethers of Formula I. A (substituted) 4-nitrophenol (1) is reacted with an activated tertiary amine in the presence of a base in a suitable solvent. The activating group may be halogen or a sulfonate ester. Suitable bases are sodium hydroxide, potassium carbonate, sodium hydride or sodium alkoxides. Suitable solvents are tetrahydrofuran, acetone, methanol, ethanol, dimethylformamide, or 1,2-dimethoxyethane. The choice of the base/solvent combination will be apparent to those skilled in the art. The reaction temperature may range from 0° C. to about 150° C., preferably at about 60° C. The amino ether (2) so prepared may be synthesized in other ways. The nitrophenol may be reacted with a di-activated alkylene moiety under conditions similar to those described above. The resulting activated alkyl ether (3) may be reacted with an excess of secondary amine in an appropriate solvent such as tetrahydrofuran, acetonitrile, methanol, ethanol, dimethylformamide, at a temperature of from 0° C. to 150° C., preferably at 60° C. to 80° C. to provide the aminoalkyl ether (2). In yet another method a hydroxyalkyl tertiary amine may be reacted with a substituted 4-fluoronitrobenzene (4) under the basic conditions described above to give the aminoalkyl ether (2).

The nitro compounds (2) can be converted to the corresponding anilines by a variety of techniques which will be dependent on the various substituents. For example, the aniline (5) may be obtained by hydrogenation of (2) over a suitable catalyst—palladium on carbon, platinum oxide, Raney-nickel—in a solvent such as water, methanol, ethanol at pressures from 1 to about 4 atmospheres and temperatures at from 0° C. to 50° C. preferably around 25° C. In an alternative procedure the nitro compound (2) may be reduced to the corresponding aniline (5) by treatment with stannous chloride dihydrate in refluxing ethanol or ethyl acetate. The sulfonamides of Formula I are prepared by the reaction of aniline (5) with methanesulfonyl chloride or methanesulfonic anhydride in a suitable solvent (methylene chloride, chloroform, acetonitrile) at a temperature of from 70° C. to 110° C., which will be dependent on the reagent employed. A base (e.g., pyridine, triethylamine) may be added to the mesylation reaction mixture to facilitate the reaction.

Scheme B

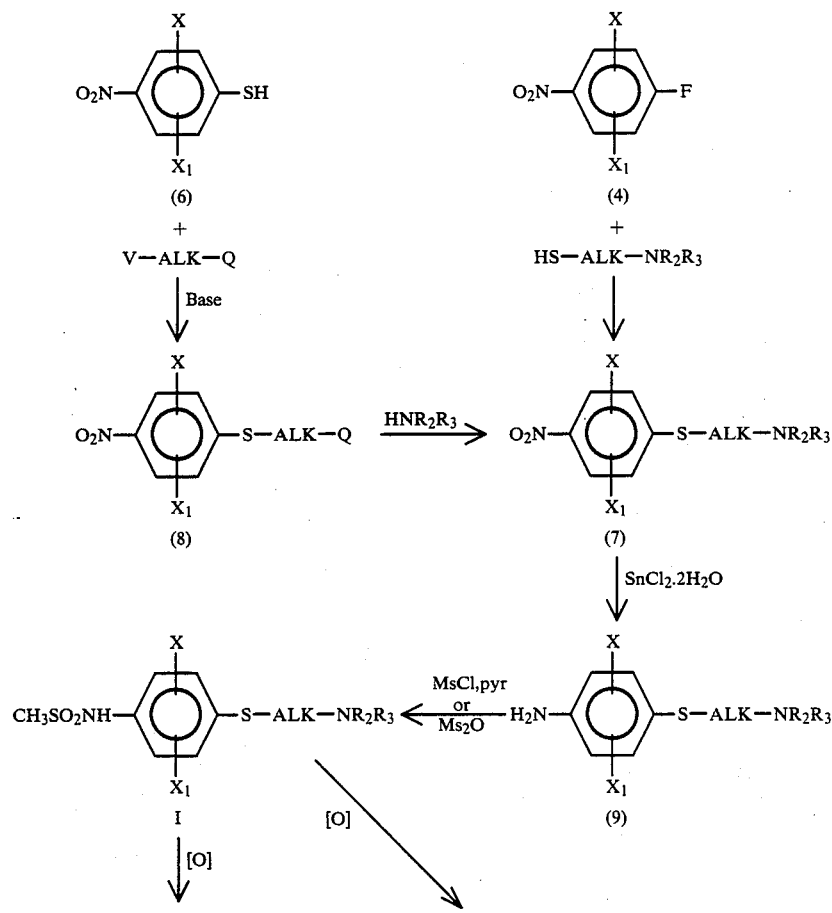

Scheme B

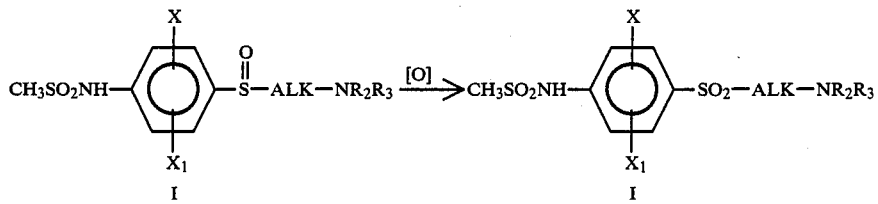

The preparation of the phenyl thioethers of Formula I, e.g., where A is —S—, is outlined in the foregoing Scheme B. The compounds are prepared under analogous conditions employed in Scheme A with the appropriate substitution of the nitrophenyl thioether (7), chemical means such as stannous chloride should be employed as hydrogenation catalyst may be poisoned by the sulfur.

The sulfoxides (A=SO) and sulfones (A=SO$_2$) of Formula I may be prepared from the corresponding thioethers. Additionally, the sulfones may be prepared from the corresponding sulfoxides by a variety of oxidation techniques. Such techniques may employ hydrogen peroxide, peracids or sodium periodate in solvents such as methanol, ethanol or acetic acid. Other than the oxidations illustrated in Scheme B—the oxidation may also take place earlier in the sequence—e.g. the oxidation of 8 —if so desired.

In order to obtain the compounds of Formula I wherein one of R$_2$ or R$_3$ is hydrogen it will be necessary to have either NR$_2$ or NR$_3$ suitably protected with an agent which may be removed at the end of the synthetic sequence.

The following schemes C and D, are illustrative of the preparation of the compounds of Formula I wherein A is
These schemes are analogous to Schemes A and B and will be apparent to those skilled in the art.

Scheme C

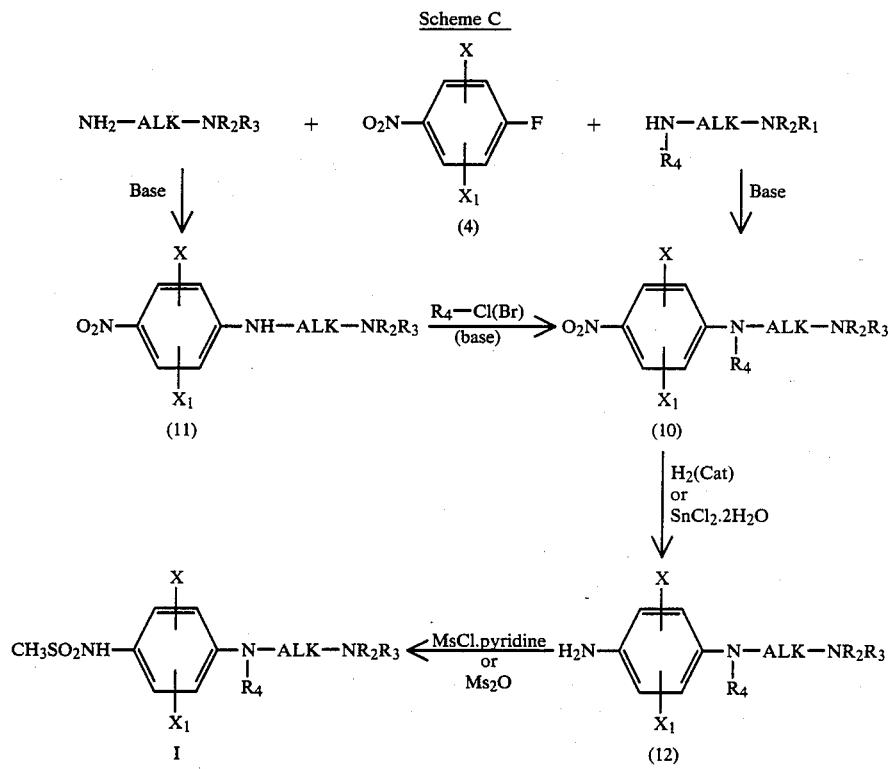

NOTE:
NR$_2$R$_3$ may be replaced by NR$_2$R$_{prot}$ where R$_{prot}$ is a protecting group which can be removed after the sulfonation step to give NR$_2$R$_3$ where R$_3$ is hydrogen.

In the approach as illustrated in the foregoing Scheme C, a substituted 4-fluoronitrobenzene is reacted with an appropriate primary or secondary alkanediamine. The reaction is generally carried out either neat or in an aprotic solvent such as acetonitrile, propionitrile or N,N-dimethylforamide under a nitrogen atmosphere at a temperature from about 25° C. to about 150° C., preferably at about 60° C. Reduction of the nitro group with the stannous chloride dihydrate is usually carried out according to the procedure of Bellamy and Ou (Tetrahedron Lett. 1984, 25, 839).

Scheme D

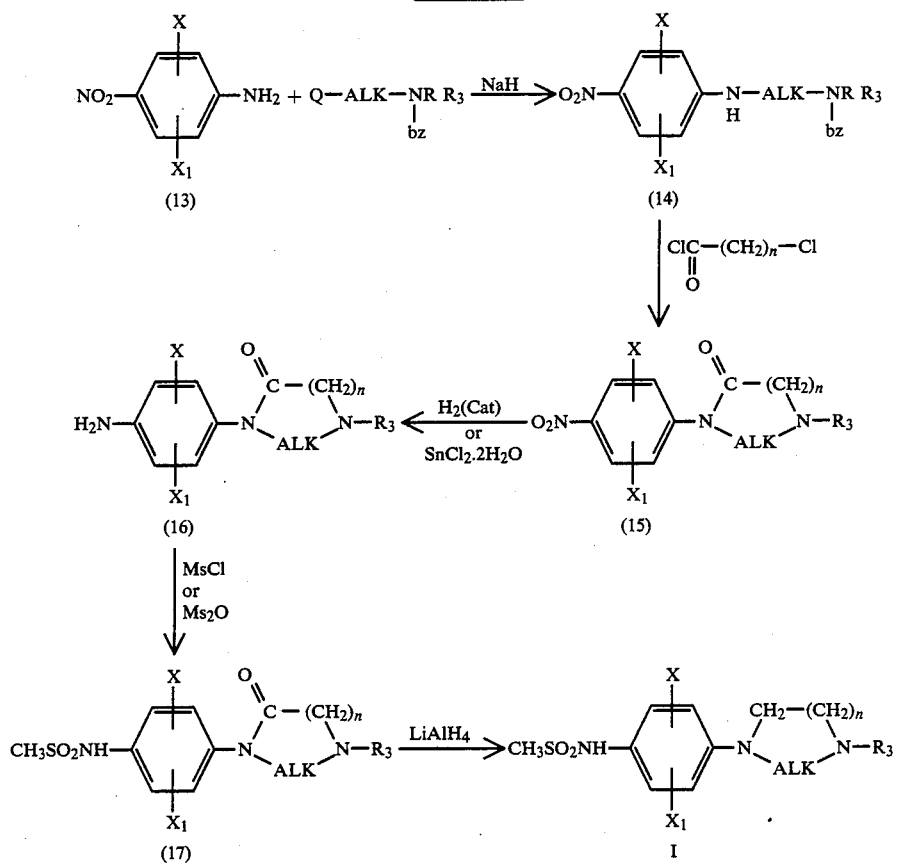

Note:
$R_3 \neq H$
bz = benzyl

The route outlined in the foregoing Scheme D is illustrative of a method where $R_2$ and $R_4$ form a ring but where $R_3$ cannot be H.

Substituted nitroaniline (13) is reacted with an activated alkylamine which contains the protecting group benzyl using sodium hydride as base in suitable solvent such as toluene, tetrahydrofuran, dimethoxyethane in a nitrogen atmosphere at a temperature from about 50° C. to 150° C., preferably at about 100° C. to give compound (14). Compound (14) is then reacted with a chloroalkanoyl chloride in a solvent such as acetonitrile or propionitrile to produce the cyclised compound (15). Reduction of compound (15) to compound (16) followed by mesylation to compound (17), which is reduced with lithium aluminum hydride to yield the compounds of Formula I, where $R_2$ & $R_4$ form a ring but where $R_3$ is not hydrogen.

The preparation of compounds wherein X or $X_1$ represents a group of the generic formula

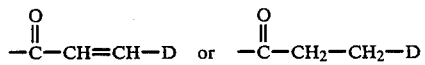

is outlined in Scheme E.

Scheme E

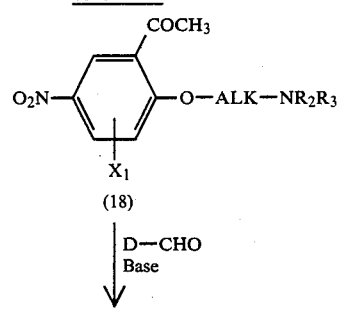

Scheme E

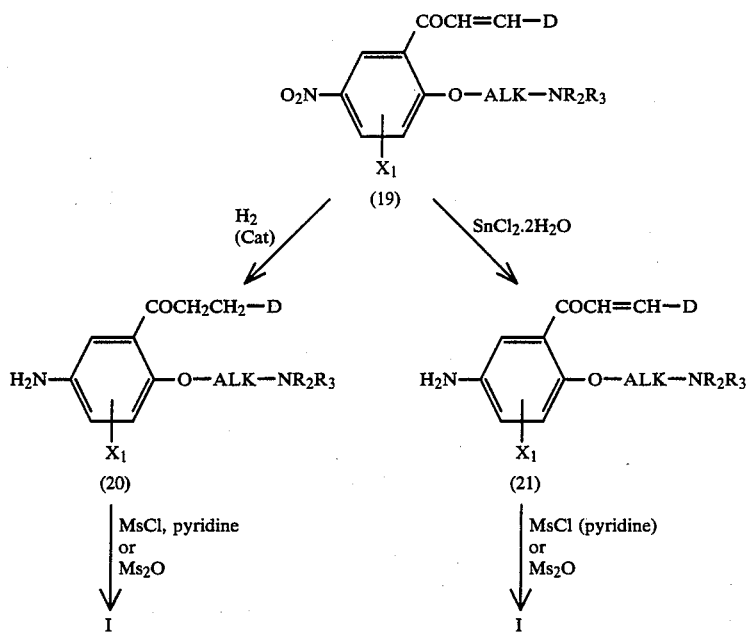

$X_1 = H$

There may be one or more asymmetric centers present in the compounds of this invention so that at least one or more pairs of optical isomers are possible. The individual optical isomers can be obtained from a racemic modification by standard procedures such as forming a salt with an optically active acid followed by selective crystallization. Where more than one racemic modification is possible for a compound, separation is accomplished by the usual methods such as chromatography or selective crystallization. Alternatively, it is possible to obtain optically active products by the use of optically active starting materials.

Method-of-Use and Pharmaceutical Composition Aspect

The novel N-[4-(aminosubstituted)phenyl]methanesulfonamides of the general Formula I of this invention and their pharmaceutically acceptable salts are useful in the treatment of various cardiovascular disorders. More especially, they find usefulness as antiarrhythmic, antiischemic, antihypertensive and vasodilator agents. Most especially when utilized as antiarrhythmic agents, these compounds will demonstrate their utility as Class III antiarrhythmic agents. Still further, some compounds will be useful as antianxiety agents.

For whatever therapeutic indication is considered, the compounds of this invention can be formulated in a therapeutically effective pharmaceutical composition and may be administered orally or parenterally. The dosage administered will be dependent on the subject being treated, the route of administration and the type and severity of the arrhythmia or other cardiac/cardiovascular event being prevented or reduced.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention in the amount of about 1 to about 500 mg. Such formulation can be administered orally at the dose of about 1 to 4 capsules per day or more often as needed, depending upon the particular condition and subject being treated. For parenteral administration a compound of this invention can be formulated as an intramuscular or intravenous medicament but is not limited thereto. In the case of treatment of a patient suffering from severe cardiac arrhythmias, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water, saline solution, and buffered aqueous solutions which may contain dispersing and surface active agents if necessary. A typical formulation suited to intravenous or intramuscular administration may contain one of the compounds of this invention in the amount of about 50 to 150 mg and a solubilizing agent and sufficient sterile water to bring the volume to about 5 mL-100 mL. Such formulation can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The pharmaceutical preparations of the compounds of this invention may optionally, additionally contain one or more other pharmaceutically active substances wherein the compounds are of differing intrinsic activity. Some of the substances envisioned are vasodilators such as glycerol trinitrate, pentaerythritol tetranitrate and carbochromen: diuretic agents, such as chlorothiazide; heart tonics, such as digitalis preparations; hypotensive agents, such as Rauwolfia alkaloids and guanethidine; bronchodilators and sympathomimetic agents, such as isoprenaline, orciprenaline, adrenalin and ephedrine; α-adrenergic blocking agents, such as phentolamine; β-adrenergic blocking agents, such as propranolol and other antiarrhythmic agents such as quinidine.

This invention described hereinabove is illustrated below in the Preparations and Examples, which, however, is not to be construed as limiting the scope of this invention.

PREPARATIONS

Preparation 1

N,N-Diethyl-N'-(4-nitrophenyl)-1,2-ethanediamine hydrochloride

To 8.3 g (71 mmol) of N,N-diethylethylenediamine under nitrogen atmosphere add 6.6 g (47 mmol) of 4-fluoronitrobenzene. Stir the mixture at ambient temperature for 1 day and heat at 45° C. for 4 h. Upon completion of the reaction add 100 mL of $CH_2Cl_2$ and 100 mL 1M HCl. Separate the layers and add 50% sodium hydroxide to the aqueous layer until it is basic. Extract the aqueous layer with $2 \times 100$ mL $CH_2Cl_2$, dry the organics over anhydrous $Na_2SO_4$. Remove drying agent by filtration and remove solvent in vacuo. Dissolve the residue in methanolic HCl and remove the solvent in vacuo. Recrystallize the solid from EtOH to afford the title compound.

NMR (DMSO-$d_6$): (300 MHz) $\delta = 1.22(t,6)$, 3.1–3.3(m,6), 3.63(q,2), 6.77(d,2), 7.6(t,1), 8.04(d,2) and 10.6(br, 1) ppm.

Preparation 2

2-Diethylamino-N-[4-[(methylsulfonyl)amino]phenyl]-acetamide

To 100 mL of acetic acid under a nitrogen atmosphere add 12.9 g (69 mmol) of N-(4-aminophenyl)methanesulfonamide and 9.4 g (83 mmol) of chloroacetyl chloride. Stir the reaction mixture at ambient temperature. Monitor the progress of the reaction by thin-layer chromatography on silica gel ($CH_2Cl_2$ MeOH, 19:1). Upon completion of the reaction, add 300 mL of $H_2O$ and suction filter the resulting solid. To 50 mL of EtOH is added 7.0 g (27 mmol) of the solid, 9.9 g (0.14 mol) of diethylamine, and 1 g of NaI. Stir the reaction mixture at ambient temperature. Monitor the progress of the reaction by thin-layer chromatography on silica gel ($CHCl_3$:MeOH, 9:1). Upon completion of the reaction remove the solvent in vacuo. To the resulting oil add 50 mL of $H_2O$ and 100 mL EtOAc. Separate the layers and dry the organic layer over anhydrous $Na_2SO_4$. Remove the drying agent by filtration and remove the solvent in vacuo. Chromatograph the resulting oil on 50 g of silica gel with $CH_2Cl_2$:MeOH, 19:1. Combine the product fractions and remove the solvent in vacuo. Dissolve the residue in methanolic HCl and remove the solvent. Triturate the solid with EtOAc to afford the title compound.

NMR (DMSO-$d_6$) (300 MHz) $\delta = 1.24(t,6)$, 2.95(s,3), 3.24(m,4), 4.13(s,2), 7.21(d,2), 7.59(d,2), 9.69(s,1), and 9.75(br 2,1)ppm.

Preparation 3

1-(4-Nitrophenyl)-4-(Phenylmethyl)Piperazine.

To a solution of 48.67 g (0.35 mol) of 1-fluoro-4-nitrobenzene and 67.15 g (0.38 mol) of 1-benzylpiperazine in 600 mL of acetonitrile, add 52.65 g (0.381 mol) of anhydrous potassium carbonate. Heat the reaction mixture to reflux for 20h under nitrogen. After this time, add 300 mL of water and concentrate mixture to 500 mL volume. Extract the mixture with $3 \times 500$ mL of methylene chloride. Remove the solvent of the combined organic layers in vacuo. Triturate the resulting crystalline residue with 1000 mL of diethyl ether and filter to obtain title compound.

NMR (CDCl3) $\delta = 2.59(t,4)$, 3.42(t,4), 3.57(s,2), 6.80(d,2), 7.34(m,5) and 8.11(d,2)ppm.

Preparation 4

4-L4-Phenylmethyl-1-piperazinyl]benzenamine

To a solution of 85 g (0.29 mol) of 1-(4-nitro-phenyl)-4-(phenylmethyl)piperazine in 500 mL of ethanol, add 325.2 g (1.44 mol) of tin(11) chloride dihydrate. Heat the reaction mixture to reflux for 20h. After this time, pour reaction mixture over a slurry of 200 g of sodium bicarbonate and 200 mL of water. Stir slurry for 5 minutes and decant off the ethanol. Add 1000 mL of ethyl acetate to slurry and stir for 5 minutes. Decant away ethyl acetate and combine with ethanol. Wash this solution with a solution of 500 mL of saturated sodium chloride solution and 100 mL of saturated sodium bicarbonate solution. Dry the organic phase over anhydrous $Na_2SO_4$. Remove the solvent in vacuo. Triturate the resulting crystalline compound with 1000 mL of diethyl ether and filter to obtain the title compound.

NMR (CDCl3): $\delta = 2.61(t,4)$, 3.06(t,4), 3.34(br, 2), 3.57(s,2), 6.63(d,2), 7.80(d,2), 7.22–7.40(m,5)ppm.

Preparation 5

1-Methyl-4-(4-nitrophenyl)piperazine 1.1 hydrochloride

To a solution of 25.0 g (0.18 mol) of 1-fluoro-4-nitrobenzene and 19.5 g (0.2 mol) of 1-methylpiperazine in 300 mL of acetonitrile, add 48.9 g (0.35 mol) of anhydrous potassium carbonate. Heat the reaction mixture to 60° C. for 20 h under nitrogen. After this time, add 100 mL of water and concentrate mixture to 200 mL volume. Add another 100 mL of water and extract with $3 \times 200$ mL of methylene chloride. Extract the combined methylene chloride extracts with 100 mL of 6N hydrochloric acid solution and $3 \times 200$ mL of water. Make the combined aqueous extracts basic (pH=14) with 50% sodium hydroxide solution and extract with $3 \times 200$ mL of methylene chloride. Dry the extracts over anhydrous sodium sulfate. Remove the drying agent by filtration and evaporate the solvent in vacuo. Dissolve the residue in 150 mL of methanol and bubble hydrogen chloride gas through the solution until pH=1. Precipitate the product by addition of diethyl ether to obtain the title compound.

NMR (D2O): $\delta = 3.01(s,3)$, 3.11–3.51(br, 4), 3.51–3.82 (br,2), 3.98–4.28(br,2), 6.99(d,2) and 8.07(d,2)ppm.

Preparation 6

4-[4-Methyl-1-piperazinyl]benzenamine dihydrochloride

Hydrogenate a solution of 37.0 g (0.14 mol) of 1-methyl-4-(4-nitrophenyl)piperazine 1.1 hydrochloride in 1.5 L of 50% aqueous ethanol over 1.85 g of 10% palladium on carbon catalyst at 50 psi. At the completion of the reaction remove the catalyst by filtration and evaporate the solvent in vacuo. Dissolve the residue in 500 mL of methanol and acidify the solution to pH=1 with hydrogen chloride gas. Filter the resulting solid to obtain the title compound.

NMR ($D_2O$) δ=2.97(s,3), 3.08–3.35(m,4), 3.66(d,2), 3.89(d,2), 7.19(d,2) and 736(d,2)ppm.

Preparation 7

N-L-4-[(Phenylmethyl)amino]Phenyl]methanesulfonamide

To 100 mL methanol under a nitrogen atmosphere add 18.0 g (96.7 mmol) of N-(4-aminophenyl)methanesulfonamide, 10 g (98 mmol) of benzaldehyde, and 6.3 g (0.10 mol) of sodium cyanoborohydride. The solution is acidified to pH=6.5 with concentrated HCl. Monitor the progress of the reaction by thin-layer chromatography on silica gel (methylene chloride:methanol, 19:1). Upon completion of the reaction, concentrated HCl is added to the reaction until gas evolution ceases. Water and ethyl ether are added and the layers separated. To the aqueous layer add saturated aqueous sodium bicarbonate until pH of 9 is reached. Extract the aqueous layer with 2×100 mL acetate. Combine the extracts and dry over anhydrous sodium sulfate. Remove drying agent by filtration and remove solvent in vacuo. Recrystallize the residue from ethanol to yield the title compound.

NMR (DMSO-$d_6$): δ=2.80(s,3), 4.23(d,2), 6.25(t,1), 6.54(d,2) 6.92(d,2) 7,2–7.4(m,5) and 8.94(br,1)ppm.

Preparation 8

2-Chloro-N-[4-](methylsulfonyl)amino]phenyl]-N-(phenylmethyl)acetamide

To 100 mL of acetic acid under nitrogen add 19.4 g (70.3 mmol) of N-[4-[(phenylmethyl)amino]phenyl]methanesulfonamide and 9.9 g (88 mmol) of chloroacetyl chloride. Monitor the progress of the reaction by thin-layer chromatography on silica gel (methylene chloride:methanol, 9:1). Upon completion of the reaction, add 400 mL of water. Collect the resulting solid by filtration and recrystallize from ethanol to yield the title compound.

NMR (DMSO-$d_6$) δ=3.02(s,3), 4.09(s,2), 4.85(s,2), 7.1–7.4(m,9) and 9.90(br,1)ppm.

Preparation 9

2-(Diethylamino)-N-[4-[(methylsulfonyl)amino]-Phenyl]-N-(Phenylmethyl)acetamide E-butenedioic acid salt (1:1)

To 150 mL of ethanol under a nitrogen atmosphere add 15 g (42 mmol) of 2-chloro-N-[4-[methylsulfonyl)amino]phenyl]-N-(phenylmethyl)acetamide, 21 g (0.28 mol) of diethylamine and 1 g (7 mmol) of sodium iodide. Stir the reaction mixture at ambient temperature. Monitor the progress of the reaction by thin-layer chromatography on silica gel (methylene chloride:methanol, 9:1). Upon completion of the reaction add 200 mL of water. Extract the aqueous solution with 2×100 mL of ethyl acetate. Combine the extracts and dry over anhydrous sodium sulfate. Remove drying agent by filtration and evaporate solvent in vacuo. Dissolve resulting oil in methanol and add fumaric acid. Remove solvent in vacuo and recrystallize from 2-propanol to afford the title compound.

99(s,3),

NMR (DMSO-$d_6$) δ=0.87(t,6), 2.59(q,4), 2. 3 20(br s,2), 3.2–5.4(br,2), 4.82(br s,2), 6.59(s,2), 7.1–7.4(m,9) and 9.9(br s,1)ppm.

Preparation 10

1-Ethyl(phenylmethyl)amino-3-(2-methylpropoxy)-2-propanol

To 100 mL (1.1 mol) of isobutanol under nitrogen atmosphere add 59 g (0.64 mol) of epichlorohydrin and $ZnCl_2$ (1 mL of a 0.872 M solution in $Et_2O$) Stir the reaction mixture at 100° C. for two days, then cool to room temperature and add 91 g (0.67 mol) of ethyl(phenylmethyl)amine and 100 mL of 50% aqueous NaOH. Resume heating for an additional three h. Add water and extract twice with $Et_2O$. Combine the organic layers and dry over anhydrous $Na_2SO_4$. Remove the drying agent by filtration and remove the solvent in vacuo. Distillation of the residue (130° C. at 0.4 mm of Hg) provides the title compound.

NMR ($CDCl_3$) (300 MHz) δ=0.89(d,6), 1.04(t,3), 1.86(m,1), 2.5(m,4), 3.21(d,2), 3.4(m,3), 3.48(d,1), 3.77(d,1), 3.84(m,1), 7.32(m,5)ppm.

Preparation 11

2-Chloro-N-ethyl-3-(2-methylpropoxy)-N-(phenylmethyl)-1-propanamine

To 50 mL of $CHCl_3$ under a nitrogen atmosphere add 28 g (0.23 mol) of thionyl chloride and 31 g (0.12 mol) of 1-ethyl(phenylmethyl)amino-3-(2-methylpropoxy)-2-propanol. Reflux the reaction mixture for ca. 4h, then cool to room temperature. Add 2N aqeuous NaOH until the mixture is basic and extract twice with $Et_2O$. Combine the organic layers and dry over anhydrous $NaSO_4$. Remove the drying agent by filtration and remove the solvent in vacuo. Distillation of the residue provides the title compound.

NMR ($CDCl_3$) (30 MHz) δ=1.0(d,6), 1.12(t,3), 1.9(m,1), 2.65(quar,2), 2.87(m,2), 3.38(d,2), 3.7(m,4), 4.0(m,1), 7.3(m,5)ppm.

Preparation 12

$N^2$-Ethyl-3-(2-methylpropoxy)-N1-(4-nitrophenyl)-$N^2$-(phenylmethyl)-1,2-propanediamine To 100 mL of toluene under a nitrogen atmosphere add 7.2 g (60% in mineral oil, 0.18 mol) of NaH, 13 g (96 mmol) of 4-nitroaniline, and 25 g (88 mmol) of 2-chloro-N-ethyl-3-(2-methylpropoxy)-N-(phenylmethyl)-1-propanamine. When the addition is complete stir the reaction at 105° C. Monitor the progress of the reaction by thin-layer chromatography on silica gel (ethyl acetate:hexane, 1:1). Upon completion of the reaction add water. Extract the aqueous layer with $Et_2O$. Combine the extracts, wash with water, and dry over anhydrous $Na_2SO_4$. Remove the drying agent by filtration and remove the solvent in vacuo. Chromatography of the resulting oil on silica gel with ethyl acetate:hexane, 1:4 affords the title compound.

NMR ($CDCl_3$): δ=0.94(d,6), 1.08(t,3), 1.88(m,1), 2.68(m,2), 3.0–3.3(m,5), 3.52(dd,1), 3.60(d,1), 3.71(dd,1), 3.37(br,1), 6.48(d,2) and 8.10(d,2)ppm.

Preparation 13

4-Ethyl-5-L(2-methylpropoxy)methyl]-1-(4-nitrophenyl)-2-piperazinone

To 100 mL acetonitrile under a nitrogen atmosphere add 27.8 g (72 mmol) of N²-ethyl-3-(2-methylpropoxy)-N¹-(4-nitrophenyl)-N²-(phenylmethyl)-1,2-propanediamine and 8.9 g (79 mmol) of chloroacetyl chloride. When the addition is complete, stir the reaction at reflux. Monitor the progress of the reaction by thin-layer chromatography on silica gel (hexane:ethyl acetate, 1:1). Upon completion remove the solvent in vacuo and add methylene chloride (100 mL) and saturated aqueous NaHCO₃ (100 mL). Stir the two phase mixture for one day and separate the layers. Remove the solvent from the organic phase and redissolve it in 50 mL propionitrile. Stir the reaction at reflux. Monitor the progress of the reaction by thin-layer chromatography on silica gel (hexane:ethyl acetate, 1:1). Upon completion remove the solvent in vacuo and chromatograph the residue on silica gel with hexane:ethyl acetate to give the title compound.

NMR (CDCl₃): (300 MHz) $\delta=0.87$(d,6), 1.16(t,3), 1.87(m,1), 2.68(m,1), 2.84(m,1), 3.2(m,3), 3.42(d,1), 3.6(m,3), 3.89(m,2), 7.62(d,2) and 8.28(d,2)ppm.

Preparation 14

N-[4-[4-Ethyl-5-](2-methylpropoxy)methyl]-2-oxopiperazin-1-yl[phenyl]methanesulfonamide hydrochloride To 100 mL of ethanol under nitrogen atmosphere add 16 g (48 mmol) of 4-ethyl-5-[(2-methylpropoxy)methyl]-1-(4-nitrophenyl)-2-piperazinone and 50 g (0.22 mol) of stannous chloride dihydrate. When the addition is complete, stir the reaction at reflux. Monitor the progress of the reaction by thin-layer chromatography on silica gel (ethyl acetate:hexane, 1:1). Upon completion of the reaction cool the reaction to room temperature and add saturated aqueous NaHCO₃ until basic. Remove the precipitate by suction filtration through celite and wash the residue with ethyl acetate. Separate the organic layer and dry over anhydrous Na₂SO₄. Remove the drying agent by filtration and remove the solvent in vacuo. To the resulting oil add 100 mL of acetonitrile and 8.3 g (48 mmol) of methanesulfonic anhydride. When the additions are complete, stir the reaction at reflux for 4 hours. Upon completion of the reaction, remove the solvent in vacuo and dissolve the residue in CH₂Cl₂ and saturated aqueous NaHCO₃. Separate the organic layer and dry it over anhydrous Na₂SO₄. Remove drying agent by filtration and evaporate the solvent in vacuo. Chromatograph the oil on silica gel (CH₂Cl₂ MeOH, 25:1). Combine the product fractions and evaporate the solvent in vacuo. Dissolve the residue in methanolic HCl and remove the solvent in vacuo. Recrystallize from acetonitrile/ether to give the title compound.

NMR (DMSO-d₆): (300 MHz)$\delta=0.84$(d,6), 1.32(t,3), 1.82(m,1), 3.02(s,3), 3.24(d,2), 3.4(m,1), 3.75–4.2(m,7), 7.27(m,4), 9.93(s,1) and 11.6(br,1)ppm.

Preparation 15

1-Diethyl-3-(2-methylpropoxy)-N²-4-nitrophenyl-1,2-propanediamine

To 100 mL of toluene under a nitrogen atmosphere add 8.3 g (60% in mineral oil, 0.21 mmol) of NaH, 11.2 g (81 mmol) of 4-nitroaniline, and 17.8 g (80 mmol) of 2-chloro-N,N-diethyl-3-(2-methylpropoxy)-1-propanamine. When the addition is complete, allow the reaction to stir at 115° C. Monitor the progress of the reaction by thin-layer chromatography (ethyl acetate:hexane, 1:1). Upon completion of the reaction add water. Extract the aqueous layer with ethyl acetate. Combine the extracts, wash with water, and dry over anhydrous Na₂SO₄. Remove drying agent by filtration and remove solvent in vacuo. Chromatography of the resulting oil on silica gel (ethyl acetate:hexane, 1:4) affords the title compound.

NMR (CDCl₃): $\delta=0.92$(d,6), 1.05(t,6), 1.85(m,1), 2.52(dq,2), 2.69(dq,2), 2.99(t,1), 3.1-3.2(m,3), 3.30(m,1), 3.39(dd,1), 3.61(dd,1), 5.54(br,1), 6.52(d,2) and 8.08(d,2)ppm.

Preparation 16

N-[2-Diethylamino-3-(2-methylpropoxy)]Propyl-N-[4[(methylsulfonyl)amino]phenyl]benzamide To 75 mL of CH₂Cl₂ under a nitrogen atmosphere add 8.4 g (26 mmol) of N¹,N¹-diethyl-3-(2-methylpropoxy)-N²-(4-nitrophenyl)-1,2-propanediamine, 4.0 g (39 mmol) of triethylamine, and 4.2 g (30 mmol) of benzoyl chloride. When the additions are complete, allow the reaction to stir at ambient temperature. Monitor the progress of the reaction by thin-layer chromatography (ethyl acetate:hexane, 1:1). Upon completion of the reaction, add saturated NaHCO₃ and allow the mixture to stir vigorously. After stirring for 1 h, the layers are separated and the organic layer is dried over anhydrous Na₂SO₄. Remove drying agent by filtration and remove solvent in vacuo to give an oil.

Dissolve the oil in 50 mL of ethanol under a nitrogen atmosphere and add 40 g (0.18 mol) of stannous chloride dihydrate When the addition is complete, allow the reaction to stir at reflux. Monitor the progress of the reaction by thin-layer chromatography (ethyl acetate: hexane, 1:1). Upon completion of the reaction remove the heat source and add saturated NaHCO₃ until basic. Remove the precipitate by suction filtration through celite and wash the residue with ethyl acetate. Separate the organic layer and dry over anhydrous Na₂SO₄. Remove the Na₂SO₄ by filtration and remove the solvent in vacuo. Filter the resulting oil through a plug of silica with CH₂Cl₂:MeOH (19:1) and remove the solvent in vacuo. To the resulting oil add 20 mL of acetonitrile and 3.7 g (21 mmol) of methanesulfonic anhydride. When the additions are complete, stir the reaction at reflux for 5 h. Upon completion of the reaction, remove the solvent in vacuo and dissolve the residue in CH₂Cl₂ and saturated aqueous NaHCO₃. Separate the organic layer and dry it over anhydrous Na₂SO₄. Remove the drying agent by filtration and remove the solvent in vacuo. Chromatograph the oil on silica gel CH₂Cl₂ MeOH, 25:1 to provide the title compound.

NMR (CDCl₃) (80 MHz) $\delta=0.90$(d,6), 0.95(t,6), 2.80(m,1), 2.5–3.0(m,5), 2.82(s,3), 3.10(d,2), 3.0–3.6(m,3), 4.0(m,1) and 7.0–7.3(m,10)ppm.

Preparation 17

N-[2-(Cyclopentyl)ethyl]benzenemethanamine

Combine 10.7 g (0.1 mol) of benzenemethanamine and 17.7 g (0.1 mol) of (2-bromoethyl)cyclopentane in 100 mL of acetonitrile. Heat the mixture to reflux and follow the progress of the reaction by thin-layer chromatography on silica gel. At the completion of the reaction remove the solvent in vacuo and add 100 mL of saturated sodium bicarbonate solution. Extract the aqueous mixture with three 100 mL portions of diethyl ether. Dry the combined extracts over anhydrous sodium sulfate. Filter the drying agent and remove the solvent in vacuo to obtain the title compound.

Preparation 18

N-[2-(Cyclopentyl)ethyl]-N-phenylmethyl-1,3-propanediamine

Combine 20.3 g (0.1 mol) N-[2-(cyclopentyl)ethyl] benzenemethanamine and 26.8 g (0.1 mol) of N-(3-bromopropyl)phthalimide in 100 mL of acetonitrile. Heat the reaction mixture at reflux and monitor the progress of the reaction by thin-layer chromatography on silica gel. At the completion of the reaction remove the solvent in vacuo. To the residue add 100 mL of ethanol and 15 g (0.3 mol) of hydrazine hydrate. Reflux the reaction mixture and follow the progress of the reaction by thin-layer chromatography on silica gel. At the completion of the reaction, cool the mixture and add 50 mL of 4N hydrochloric acid. Reflux the mixture for ca. 15 min. then cool to room temperature. Filter the resulting solid. Evaporate the filtrate in vacuo, then add 100 mL of 4N sodium hydroxide solution (pH 11). Extract the aqueous mixture with four 100 mL portions of methylene chloride. Combine the organic extracts and dry over anhydrous sodium sulfate. Remove the drying agent by filtration and evaporate the solvent in vacuo to obtain the title compound.

Preparation 19

N-[2-(Cyclopentyl)ethyl]-N'-(4-nitrophenyl)-N-phenylmethyl-1,3-propanediamine

In a manner similar to Preparation 1 react 4-fluoro1-nitrobenzene with N-[2-(cyclopentyl)ethyl]-N-phenylmethyl-1,3-propanediamine to obtain the title compound.

Preparation 20

4-[2-(Cyclopentyl)ethyl]-1-(4-nitrophenyl)-hexahydro1H-1,4-diazepin-2-one

In a manner similar to Preparation 13 react N-[2 (cyclopentyl)ethyl]-N'-(4-nitrophenyl)-N-(phenylmethyl)1,3-propanediamine with chloroacetyl chloride to obtain the title compound.

Preparation 21

N-[4-[4-[(2-(Cyclopentyl)ethyl]hexahydro-2-oxo-1H-1,4-diazepin-1-yl]phenyl]methanesulfonamide In a manner similar to Preparation 14 react 4-[2(cyclopentyl)ethyl]-1-(4-nitrophenyl)hexahydro-1H-1,4-diazepin-2-one with Tin(11) chloride dihydrate in ethanol, then with methanesulfonic anhydride in acetonitrile to obtain the title compound.

Preparation 22

1-(Phenylmethyl)-3-pyrrolidinemethanol

In a manner similar to Preparation 7 react 3-pyrrolidinemethanol with benzaldehyde to obtain the title compound.

Preparation 23

N-(2,6-Dimethyl-4-nitrophenyl)-1-phenylmethyl-3-pyrrolidinemethanamine

To a solution of 19.1 g (0.1 mol) 1-(phenylmethyl)-3pyrrolidinemethanol in 100 mL of dry pyridine cooled to -10° C. under a nitrogen atmosphere add slowly 20 g (0.11 mol) of p-toluenesulfonyl chloride such that the temperature does not exceed 0° C. Stir the mixture overnight at 0° -10° C. Pour the reaction mixture onto 300 mL of diethyl ether, then wash the solution with three 50 mL portions of water. Dry the organic phase over anhydrous sodium sulfate. Filter the drying agent and evaporate the solvent in vacuo to obtain the tosylate. React the tosylate with 2,6-dimethyl-4-nitroaniline in a mannner similar to Preparation 12 to obtain the title compound.

Preparation 24

N-(4-Nitrophenyl)-4-oxo-N-(phenylmethyl)hexanamide

To a solution of 22.8 g (0.1 mol) of 4-nitro-N-(phenylmethyl)benzenamine and 7.9 g (0.1 mol) of pyridine in 150 mL of methylene chloride cooled to 0° C. add slowly a solution of 16.3 g (0.11 mol) of 4-oxohexanoyl chloride (prepared from the acid and thionyl chloride or oxalyl chloride). When the addition is complete stir the solution and allow to warm slowly to room temperature. Follow the progress of the reaction by thin-layer chromatography on silica gel. At the completion of the reaction wash the solution with two 25 mL portions of 5% hydrochloric acid solution, two 25 mL portions of 5% sodium carbonate solution and 50 mL of saturated sodium chloride solution. Dry the organic phase over anhydrous sodium sulfate. Remove the drying agent by filtration and evaporate the solvent in vacuo to obtain the title compound.

Preparation 25

N-[4-L(methylsulfonyl)amino]phenyl]-4-oxo-N-(phenylmethyl)hexanamide In a manner similar to Preparation 14 react N-(4-nitrophenyl)-4-oxo-N-(phenylmethyl)hexanamide with tin (II) chloride dihydrate in ethanol, then with methanesulfonic anhydride in acetonitrile to obtain the title compound.

Preparation 26

2-(Cyclohexyl)ethyl]amino]-N-[4-[(methylsulfonyl)-amino]phenyl]-N-(phenylmethyl)hexanamide In a manner similar to Preparation 7 react N-[4(methylsulfonyl)amino]phenyl]-4-oxo-N-(phenylmethyl)hexanamide with 2-(cyclohexyl)ethanamine and sodium cyanoborohydride in methanol to obtain the title compound.

Preparation 27

N-Ethyl-5-methylhexanamine

In a manner similar to Preparation 7 react 5-methylhexanal with ethylamine and sodium cyanoborohydride in methanol to obtain the title compound.

Preparation 28

N-Ethyl-N-(5-methylhexyl)-1,2-ethanediamine

In a manner similar to Preparation 18 react N-ethylmethylhexanamine with N-(2-bromoethyl)phthalimide, then with hydrazine in ethanol to obtain the title compound.

Preparation 29

N-Ethyl-N-(5-methylhexyl)-N'-(4-nitrophenyl)-1,2-ethanediamine

In a manner similar to Preparation 1 react N-ethyl N-(5-methylhexyl)-1,2-ethanediamine with 4-fluoro-1-nitrobenzene to obtain the title compound.

Preparation 30

N-Ethyl-N-(5-methylhexyl)-N'-(4-nitrophenyl)-N'-(2-propenyl)-1,2-ethanediamine In a manner similar to Preparation 12 react N-Ethyl-N-(5-methylhexyl)-N'-(4-nitrophenyl)-1,2-ethanediamine with allyl bromide to provide the title compound.

Preparation 31

N-(4-Aminophenyl)-N'-ethyl-N'-(5-methylhexyl)-N-(2-propenyl)-1,2-ethanediamine In a manner similar to Preparation 4 react N-ethyl-N-(5-methylhexyl)-N'-(4-nitrophenyl)-N'-(2-propenyl)1,2-ethanediamine with tin(II) chloride dihydrate in ethanol to obtain the title compound.

Preparation 32

2,N-Dimethyl-N-(3-methyl-4-nitrophenyl)pyridine-4-carboxamide

To a solution of 16.6 g (0.1 mol) of 3,N-dimethyl-4-nitrobenzenamine and 10.2 g (0.1 mol) of triethylamine in mL of methylene chloride cooled to 0° C. under a nitrogen atmosphere add slowly a solution of 15.6 g (0.1 mol) of 2-methylpyridine-4-carbonyl chloride (prepared from the corresponding acid and thionyl chloride) such that the temperature is maintained between 0°-5° C. After the addition is complete, stir the mixture for 6 h and allow to warm slowly to room temperature. Quench the reaction mixture by the addition of 50 mL of water. Separate the layers and wash the organic layer with two 50 mL portions of water, two 50 mL portions of 5% sodium bicarbonate solution and 50 mL of saturated sodium chloride solution. Dry the methylene chloride solution over anhydrous sodium sulfate. Remove the drying agent by filtration and evaporate the solvent to obtain the title compound.

Preparation 33

2-[[(4-Nitrophenyl)(ethyl)amino]carbonyl]cyclopropane-1-carboxylic acid

In a manner similar to Preparation 12 react N-ethyl-4-nitrobenzenamine with sodium hydride in toluene, then with 3-oxabicyclo[3.1.0]hexane-2,4-dione [cyclopropane1,2-dicarboxylic acid anhydride]to obtain the title compound.

Preparation 34

N-Ethyl-N-(4-nitrophenyl)-N'-octyl-N'-(phenylmethyl)-cyclopropane-1,2-dicarboxamide In a manner similar to Preparation 32 react N-octyl-benzenemethanamine with 2-[[(4-nitrophenyl)(ethyl)amino]carbonyl]cyclopropane-1-carbonyl chloride (prepared from the acid and oxalyl chloride or thionyl chloride) in methylene chloride to obtain the title compound.

Preparation 35

N-Ethyl-N-[4-[(methylsulfonyl)amino]phenyl]-N'-octyl-N'-(phenylmethyl)cyclopropane-1,2-dicarboxamide In a manner similar to Preparation 14 react N-ethyl-N-(4-nitrophenyl)-N'-octyl-N'-(phenylmethyl)cyclopropane-1,2-dicarboxamide with tin(II) chloride dihydrate in ethanol, then with methanesulfonic anhydride in acetonitrile to obtain the title compound.

Preparation 36

4-[[Ethyl(4-nitrophenyl)amino]methyl]cyclohexanone

In a manner similar to Preparation 23 react 4-(hydroxymethyl)cyclohexanone with p-toluenesulfonyl chloride in pyridine to obtain the tosylate. The tosylate is further reacted with N-ethyl-4-nitrobenzenamine and sodium hydride in toluene as in Preparation 12 to obtain the title compound.

Preparation 37

N-[4-[Ethyl((4-oxocyclohexyl)methyl)amino]phenyl]-methanesulfonamide

In a manner similar to Preparation 14 react 4-[[ethyl(4-nitrophenyl)amino]methyl]cyclohexanone with tin(II) chloride in ethanol, then with methanesulfonic anhydride in acetonitrile to obtain the title compound.

Preparation 38

N,N-Diethyl-2-[(4-nitrophenyl)thio]ethaneamine

To a solution of 7.0 g (45 mmol) of 4-nitrothiophenol and 22.5 mL of 4N aqueous potassium hydroxide in 40 mL of dimethylformamide add a solution of 9.53 g (55 mmol) of 2-chloro-N,N-diethylethanamine hydrochloride in 40 mL of dimethylformamide. Heat the reaction mixture for about 3 h at 100° C. After this time, cool the mixture to room temperature and add 150 mL of water. Extract th aqueous mixture with 3×200 mL of methylene chloride. Combine the methylene chloride extracts and extract these with 200 mL of 1N aqueous hydrochloric acid. Make the acid extract basic with saturated aqueous sodium bicarbonate solution and extract this basic solution with 2×500 mL of methylene chloride. Wash the methylene chloride extracts with 100 mL of saturated aqueous sodium chloride solution and dry over anhdrous sodium sulfate. Remove the drying agent by filtration and evaporate the solvent in vacuo to obtain the title compound.

NMR (CDCl$_3$): δ=1.06(t,6), 2.64(quar,4), 2.80(t,2), 3.16(t,2), 7.39(d,2) and 8.16(d,2)ppm.

Preparation 39

4-[[2-(Diethylamino)ethyl]thio]benzenamine

To a solution of 7.4 g (29 mmol) of N,N-diethyl-2-[(4-nitrophenyl)thio]ethanamine in 150 mL of ethanol add 32.8 g (140 mmol) of tin(II) chloride dihydrate. Reflux the reaction mixture for about 5 h. After this time, cool the reaction mixture to room temperature and carefully add the mixture to a solution of 75 g (0.54 mol) of potassium carbonate in 500 mL of water. Extract the mixture with 3×500 mL of ethyl acetate. Combine the organic extracts and wash with 2×350 mL of saturated aqueous sodium chloride solution. Dry the organic extracts over anhydrous sodium sulfate. Remov the drying agent by filtration and evaporate the solvent in vacuo to obtain the title compound.

NMR (CDCl₃): δ=0.99(t,6), 2.53(quar,4), 2.67(m,2), 2.87(m,2), 3.75(br s,2), 6.61(d,2) and 7.24(d,2)ppm.

Preparation 40

1-(3-Chloropropoxy)-4-nitrobenzene

The title compound is prepared in a manner similar to that described in Organic Syntheses, Collective Volume 3, p. 140.

NMR (CDCl₃) δ=2.32 (quin,2), 3.80 (t,2), 4.26 (t,2), 7.00(d,2) and 8.23(d,2)ppm.

Preparation 41

N,N-Diethyl-3-(4-nitrophenoxy)propanamine hydrochloride

Heat 19.41 g (0.09 mol) of 1-(3-chloropropoxy)-4-nitrobenzene and 50 mL (0.48 mol) of diethylamine in 100 mL of acetonitrile at 45°–50° C. Follow the progress of the reaction by thin-layer chromatography on silica gel (acetonitrile:ammonium hydroxide, 95:5). At the completion of the reaction remove the solvent in vacuo. Dissolve the residue in 100 mL of H₂O and make the mixture acidic (pH=1) with concentrated hydrochloric acid. Extract the acidic solution with 3×100 mL of diethyl ether. Neutralize the acid solution (pH=7) with 20% aqueous sodium hydroxide solution and extract with 3×100 mL of diethyl ether. Adjust the pH of the aqueous layer to 12 with 20% aqueous sodium hydroxide solution and extract with 3×100 mL of diethyl ether. Wash the ether extracts from the basic solution with 50 mL of saturated sodium chloride solution, combine them and dry over anhydrous sodium sulfate. Remove the drying agent by filtration and evaporate the solvent in vacuo. Dissolve the residue in 100 mL of methanol and add concentrated hydrochloric acid until pH=1. Stir the solution with 2 g of charcoal, filter and remove the solvent in vacuo. Recrystallize the residue from acetonitrile to obtain the title compound.

NMR (DMSO-d₆) δ=1.23(t,6), 2.18(m,2), 3.02–3.26 (m,6), 4.24(t,2), 7.17(d,2), 8.23(d,2) and 10.42(br s,1) ppm.

Preparation 42

4-[3-(Diethylamino)propoxy)benzenamine dihydrochloride

Hydrogenate a solution of 8.5 g (29.4 mmol) of N,N-diethyl-3-(4-nitrophenoxy)propanamine hydrochloride in 100 mL of methanol over 0.92 g of 10% palladium on carbon catalyst at 40–45 psi at room temperature. When hydrogen uptake ceases remove the catalyst by filtration and add 5 mL of concentrated hydrochloric acid. Remove the solvent in vacuo. Recrystallize the residue from ethanol to obtain the title compound.

NMR (DMSO-d₆): δ=1.23(t,6), 2.16(m,2), 3.14(m,6), 4.09(t,2), 7.04(d,2), 7.33(d,2), 10.24(br s,3) and 10.60 (br s,1)ppm.

Preparation 43 trans-N,N-Diethyl-2-(4-nitrophenoxy)cyclohexanamine hydrochloride

To 0.24 g (10 mmol) of sodium hydride in 10 mL dimethylformamide cooled to 0° C. under a nitrogen atmosphere add dropwise 1.71 g (10 mmol) of trans-2-(N,N-diethylamino)cyclohexane. After the addition is complete, stir the reaction at ambient temperature for one hour, then cool the mixture to 0° C. Add dropwise a solution of 1.41 g (10 mmol) 4-fluoro-1-nitrobenzene in 5 mL dimethylformamide. After the addition is complete, stir the reaction for one hour at ambient temperature and then an additional hour at 70° C. Cool down the reaction to room temperature and add 150 mL of water. Extract with 4×50 mL of methylene chloride. Wash the extract with water and dry over anhydrous sodium sulfate. Remove the solvent in vacuo. Purify the resulting oil by column chromatography on silica gel (methylene chloride:methanol, 9:1). Combine the product fractions and evaporate the solvent. Dissolve the resulting oil in ethanol and add hydrochloric acid. Remove the solvent in vacuo and recrystallize the solid from acetone/ether to provide the title compound.

NMR (DMSO-d₆): δ=1.26–1.36 (m,6), 1.44–1.84(m,6), 2.20–2.34(m,2), 3.10–3.22(m,2), 3.24–3.36(m,2), 3.70–3.80 (m,1), 5.00–5.10(m,1), 7.31(d,2) and 8.25(d,2)ppm.

Preparation 44 trans-2-(Aminophenoxy)-N,N-diethylcyclohexylamine

A mixture of 4.0 g (13.7 mmol) of trans-N,N-diethyl-2-(4-nitrophenoxy)cyclohexanamine, 15.4 g (68.4 mmol) of tin(II) chloride dihydrate and 30 mL of ethanol is heated to reflux for thirty minutes under a nitrogen atmosphere. Pour the reaction on to ice-water and adjust the pH to 12 with potassium hydroxide. Filter the mixture through celite and extract the filtrate twice with ethyl acetate. Wash the extract with saturated sodium chloride solution and dry over anhydrous sodium sulfate. Remove the solvent in vacuo to yield the title compound.

NMR (CDCl₃): δ=1.01(t,6), 1.21–1.32(m,4), 1.68–1.76 (m,2), 1.82–1.88(m,1), 2.14–2.22(m,1), 2.56–2.77(m,5), 3.42(br s,2), 4.00(dt,1), 6.60(d,2) and 6.75(d,2)ppm.

Preparation 45

4-Methyl-1-[3-[(4-nitrophenyl)thio]propyl]piperidine

Dissolve 8.50 g (55 mmol) of 4-nitrothiophenol in 40 mL of dimethylformamide and make basic with 13.7 mL of 4N potassium hydroxide. Add 10.60 g (60 mmol) of N-[3-chloropropyl]-4-methylpiperidine and heat this solution to 100° C. for 3 h. After this time cool the reaction to room temperature. Add 200 mL of water and extract with 2×150 mL of methylene chloride. Acidify the combined organic extracts to pH=1 with 1N hydrochloric acid and extract with 4×150 mL of water. Neutralize the combined aqueous extracts with saturated sodium bicarbonate solution and extract with 3×200 mL of methylene chloride. Dry the organic extracts over anhydrous sodium sulfate. Filter the drying agent and remove the solvent in vacuo to provide the title compound.

NMR (CDCl₃): δ=0.93(d,3), 1.12–1.45(m,3), 1.65(m,2), 1.81–1.99(m,4), 2.45(t,2), 2.85(m,2), 3.08(t,2), 7.39(d,2) and 8.14(d,2)ppm.

Preparation 46

1-[3-[(4-Aminophenyl)thio]propyl]-4-methylpiperidine

Dissolve 15.5 g (0.0520 mol) of 4-methyl-1-[3-[(4-nitrophenyl)thio]propyl]piperidine in 150 mL of ethanol. Add 59.3 g (0.26 mol) of tin(II) chloride dihydrate and heat mixture to reflux for 5 h. After 5 h, cool the reaction mixture to room temperature. Pour reaction mixture over 100 g of potassium carbonate and dilute with 500 mL of water and 500 mL of ethyl acetate. Filter this suspension through celite and separate the layers. Extract the aqueous layer with 3×300 mL of ethyl acetate. Combine organic layers and dry over anhydrous sodium sulfate. Filter the drying agent and remove the solvent in vacuo to provide the title compound.

NMR (CDCl₃): δ=0.95(m,3), 1.1–2.2(m,9), 2.45(t,2), 2.80(m,4), 3.80(br s,2), 6.70(d,2) and 7.35(d,2)ppm.

Preparation 47

N-Ethyl-N-heptyl-3-(4-nitrophenoxy)propanamine hydrochloride

In a manner similar to Preparation 41 react 1-(3-chloropropoxy)-4-nitrobenzene with N-ethylheptanamine to obtain the title compound.

Preparation 48

4-[3-[Ethyl(heptyl)amino]propoxy]benzenamine dihydrochloride

In a manner similar to Preparation 42 hydrogenate N-ethyl-N-heptyl-3-(4-nitrophenoxy)propanamine hydrochloride over 10% palladium on carbon in methanol to obtain the title compound.

Preparation 49

1-Butyl-4-(3-methyl-4-nitrophenoxy)piperidine hydrochloride

In a manner similar to Preparation 43 react 1-butylpiperidin-3-ol with 5-fluoro-2-nitrotoluene to obtain the title compound.

Preparation 50

4-[4-Amino-3-methylphenoxy]-1-butylpiperidine

In a manner similar to Preparation 44 react 1-butyl-4-(3-methyl-4-nitrophenoxy)piperidine with tin(II) chloride dihydrate in ethanol to obtain the title compound.

Preparation 51

3-[(3-Methyl-4-nitrophenyl)thio]-N,N-bis-(1-methylethyl)propanamine

In a manner similar to Preparation 43 react 5-fluoro-2-nitrotoluene with 3-[bis(1-methylethyl)amino]-propanethiol to obtain the tile compound.

Preparation 52

2-Methyl-4-[[3-(bis(1-methylethyl)amino)propyl]thio]-benzenamine

In a manner similar to Preparation 39 react 3-[(3-methyl-4-nitrophenyl)thio]-N,N-bis(1-methylethyl)-propanamine with tin(11) chloride in ethanol to obtain the title compound.

Preparation 53

1-(5-Bromopentyloxy)-2,6-dichloro-4-nitrobenzene

In a manner similar to Preparation 40 react 1,5-dibromopentane with 2,6-dichloro-4-nitrophenol to obtain the title compound.

Preparation 54

5-(2,6-Dichloro-4-nitrophenoxy)-N-methyl-N-(phenylmethyl)pentanamine hydrochloride React 1-(5-bromopentyloxy)-2,6-dichloro-4-nitrobenzene with methyl(phenylmethyl)amine or benzyl(methyl)amine in a manner similar to Preparation 41 to obtain the title compound.

Preparation 55

2,6-Dichloro-4-[5-[methyl(phenylmethyl)amino]pentyloxy]benzeneamine

In a manner similar to Preparation 44 react 5-(2,6-dichloro-4-nitrophenoxy)-N-methyl-N-(phenylmethyl)-pentanamine with tin(II) chloride dihydrate to obtain the title compound.

Preparation 56

1-Butyl-2-pyrrolidinemethanol

To 10.1 g (0.1 mol) of 2-pyrrolidinemethanol and 13.8 g (0.1 mol) of potassium carbonate in 200 mL of acetonitrile add 13.7 g (0.1 mol) of butyl bromide. Heat the reaction mixture at reflux with stirring under a nitrogen atmosphere. Follow the progress of the reaction by thin-layer chromatography on silica gel. At the completion of the reaction remove the solvent in vacuo then dissolve the residue in water. Make the aqueous mixture acidic (pH=1) with concentrated hydrochloric acid. Extract the aqueous acid solution with 3×50 mL of hexanes. Make the aqueous solution basic (pH=12) with 20% sodium hydroxide solution and extract with 3×100 mL of methylene chloride. Dry the combined methylene chloride extracts over anhydrous sodium sulfate. Filter the drying agent and evaporate the filtrate in vacuo to obtain the title compound.

Preparation 57

1-Butyl-2-[(4-nitrophenoxy)methyl]pyrrolidine hydrochloride

React 1-butyl-2-pyrrolidinemethanol with sodium hydride and 1-fluoro-4-nitrobenzene in dimethylformamide in a manner similar to Preparation 43 to obtain the title compound.

Preparation 58

4-[(1-Butyl-2-pyrrolidinyl)methoxy]benzenamine

In a manner similar to Preparation 44 react 1-butyl-2-[(4-nitrophenoxy)methyl]pyrrolidine with tin(II) chloride dihydrate in ethanol to obtain the title compound.

Preparation 59

N-[2-(3,4-Dimethoxyphenyl)ethyl]trifluoroacetamide

Dissolve 50 g (0.28 mol) of 2-(3,4-dimethoxyphenyl)ethylamine in 200 mL of methylene chloride under nitrogen and cool to 0° C. in an ice-water bath. Add dropwise a solution of 48.7 mL (0.35 mol) of trifluoroacetic anhydride and stir at room temperature for 2 h. After 2 h, pour reaction mixture over 300 g of ice. Separate the layers and wash the organic layer with 3×250 mL of saturated sodium bicarbonate solution. Remove the solvent of the organic layer in vacuo. Recrystallize the residue from 200 mL of toluene and 100 mL of hexane to provide the title compound.

NMR (CDCl₃): δ=2.85(t,2), 3.63(m,2), 3.95(s,6), 6.37(br s,1), 6.73(s,1), 6.76(d, ) and 6.97(d,1)ppm.

Preparation 60

N-[2-(3,4-Dimethoxyphenyl)ethyl]-N-methyltrifluoroacetamide

Add 20.0 9 (0.07 mol) of N-[2-(3,4-dimethoxyphenyl)ethyl]trifluoroacetamide to a suspension of 3.17 g (0.08 mol) of 60% sodium hydride in 50 mL of dry tetrahydrofuran. Stir this suspension for 30 minutes at room temperature. After 30 minutes, add 6.72 mL (0.11 mol) of methyl iodide and stir at room temperature for one h. After one h, filter reaction mixture and make basic (pH=14) with 4N sodium hydroxide. Wash this mixture with 2×100 mL of water. Extract the combined aqueous washes with 2×100 mL of methylene chloride. Wash the combined organic extracts with 6N hydrochloric acid, then with 100 mL of water. Dry the organic layer over anhydrous sodium sulfate. Filter the drying agent and remove the solvent in vacuo to provide the title compound.

NMR (CDCl$_3$): $\delta$=2.87(t,2), 3.00(s,2), 3.07(s,1), 3 64(quar,2), 3.89(s,6) and 6.70–6.91(m,3)ppm.

Preparation 61

3,4-Dimethoxy-N-methylbenzeneethanamine

Dissolve 16.5 g (57 mmol) of N-[2-(3,4-dimethoxyphenyl)ethyl]-N-methyltrifluoroacetamide in a solution of 100 mL of 4N sodium hydroxide and 100 mL of methanol. Heat mixture at 60° C. for 1 h. After 1 h, cool reaction mixture to room temperature and extract with 2×200 mL of methylene chloride. Wash the combined organic extracts with saturated sodium chloride solution and dry over anhydrous sodium sulfate. Filter the drying agent and remove the solvent in vacuo to provide the crude title compound. Distill this material in vacuo to provide the title compound.

NMR (CDCl$_3$): $\delta$=2.44(s,3), 2.70–2.89(m,4), 3.88(s,3), 3.90(s,3), 6.78(s,1), 6.79(d,1) and 6.85(d,1) ppm.

Preparaion 62

3,4-Dimethoxy-N-[3-(4-nitrophenoxy)propyl]-N-methylbenzeneethanamine

In a manner similar to Preparation 56 react 3,4-dimethoxy-N-methylbenzeneethanamine with 1-(3-chloropropoxy)-4-nitrobenzene in acetonitrile to obtain the title compound.

Preparation 63

N-[3-(4-Aminophenoxy)propyl]-3,4-dimethoxy-N-methylbenzeneethanamine

React 3,4-dimethoxy-N-[3-(4-nitrophenoxy)propyl]-N-methylbenzneethanamine with tin(II) chloride dihydrate in ethanol to obtain the title compound.

Preparation 64

N,N-Diethyl-3-(2-methylpropoxy)-1-(4-nitrophenyl)-2-propanamine

To 30 mL of dimethylformamide under a nitrogen atmosphere add 3.6 g NaH (60% in mineral oil, 90 mmol), 6.5 g (47 mmol) of 4-nitrophenol, and 9.38 g (42 mmol) of 2-chloro-N,N-diethyl-3-(2-methylpropoxy)-1-propanamine. When the addition is complete allow the reaction to stir at 110° C. Monitor the progress of the reaction by thin-layer chromatography (ethyl acetate:hexane, 1:1). Upon completion of the reaction add water. Extract the aqueous layer with 2×100 mL of diethyl ether. Combine the extracts, wash with 2×50 mL 2N sodium hydroxide solution and dry over anhydrous sodium sulfate. Remove drying agent by filtration and remove solvent in vacuo. Chromatography of the resulting oil on silica gel with ethyl acetate: hexanes, 1:4 affords the title compound.

NMR (CDCl$_3$): $\delta$=0.88(d,6), 1.05(t,6), 1.84(m,1), 2.69(q,4), 3.16(dd,1), 3.62(dd,1), 3.30(m,1), 3.56(dd,1), 3.61(dd,1), 4.20(d,2), 6.99(d,2) and 8.20(d,2)ppm.

Preparation 65

N,N-Diethyl-2-(2,6-dimethyl-4-nitrophenoxy)ethanamine hydrobromide

To 9.0 g (53.8 mmol) of 2,6-dimethyl-4-nitrophenol in 100 mL of acetone add 10.0 g (58.1 mmol) of diethylaminoethyl chloride hydrochloride, 17.0 g (123.0 mmol) of potassium carbonate and 3.0 g (20.0 mmol) of sodium iodide. Heat the mixture at reflux with stirring. Monitor the progess of the reaction by thin-layer chromatography on silica gel (methylene chloride:methanol, 95:5). When the reaction is complete, remove the solvent in vacuo. Dissolve the resulting oil in water. Extract the aqueous solution four times with diethyl ether. Wash the organic phase with water, dilute sodium hydroxide, water and brine. Dry the etheral solution over anhydrous sodium sulfate. Remove the drying agent by filtration and remove solvent in vacuo. Dissolve the resulting oil in ethanol and add hydrobromic acid. Remove the solvent in vacuo and recrystallize the residue from ethanol/isopropanol to provide the title compound.

NMR (DMSO-d): $\delta$=1.28(t,6), 2.39(s,6), 3.28–3.32 (m,4), 3.58–3.60(m,2), 4.22(t,2), 8.02(s,2) and 9.54 (br s,1)ppm.

Preparation 66

4-(2-(Diethylamino)ethoxy)benzenamine

To 8.0 g (23 mmol) of N,N-diethyl-2-(2,6-dimethyl-4-nitrophenoxy)ethanamine hydrobromide in 90 mL of ethanol add 26.0 g (115 mmol) of tin(II) chloride dihydrate. Heat the mixture to reflux with stirring for 1.5 h. Cool the mixture and pour it onto ice-water. Adjust the pH to 12 by the addition of dilute sodium hydroxide. Add ethyl acetate and filter the mixture through celite. Extract the filtrate twice with ethyl acetate. Wash the extract with saturated sodium chloride solution and dry over anhydrous sodium sulfate. Remove the drying agent by filtration and emove the solvent in vacuo to yield the title compound.

NMR (CDCl$_3$): $\delta$=1.06(t,6), 2.20(s,6), 2.59–2.67 (quar,4), 2.86(t,2), 3.42(br s,2), 3.79(t,2) and 6.34 (s,2)ppm.

Preparation 67

[2-[2-(Diethylamino)ethoxy]-5-nitrophenyl]phenylmethanone hydrobromide

To 0.24 g (10 mmol) of sodium hydride in 20 mL dimethylformamide cooled to 0° C. under a nitrogen atmosphere add dropwise 1.17 g (10 mmol) of N,N-diethylaminoethanol with stirring. After the addition is complete, stir the reaction at 50° C. for 30 minutes, then cool the mixture to 0° C. Add dropwise a solution of 2.61 g (10 mmol) of 2-chloro-4-nitrobenzophenol in 10 mL of dimethylformamide. After the addition is complete, stir the reaction for two h at ambient temperature and add 100 mL of water. Extract with 4×50 mL of diethyl ether. Wash the extract with water and dry over anhydrous sodium sulfate. Remove the solvent in vacuo. Dissolve the crude product in ethanol and add hydrobromic acid. Remove the solvent in vacuo and recrystallize the solid from ethanol to provide the title compound.

NMR (DMSO-d$_6$): δ=0.99(t,6), 2.92–2.94(m,4), 3.30 (br s,2), 4.54(t,2), 7.48(d,1), 7.57(t,2), 7.73(t,1), 7.80(d,2), 8.28(d,1), 8.50(dd,1) and 9.43(br s,1)ppm.

Preparation 68

[5-Amino-2[2-(diethylamino)ethoxy]phenyl]phenyl]methanone

A mixture of 6.0 g (14.2 mmol) of [2-[2-(diethylamino)ethoxy]-5-nitrophenyl]phenylmethanone hydrobromide, 22.0 g (97.5 mmol) of tin(II) chloride dihydrate and 100 mL of ethanol is heated to reflux for one hour under a nitrogen atmosphere. Pour the reaction onto ice-water and adjust the pH to 12 with potassium hydroxide. Add ethyl acetate and filter the mixture through celite. Separate the layers of the filtrate and extract the aqueous layers twice with ethyl acetate. Wash the combined organic layers with water, saturated sodium chloride solution, and dry over anhydrous sodium sulfate. Remove the solvent in vacuo to yield the title compound.

NMR (CDCl$_3$): δ=0.87(t,6), 2.37(q,4), 2.41(t,2), 3.57(br s,2), 3.85(t,2), 6.72–6.80(m,3), 7.40(t,2), 7.53 (t,1) and 7.90(d,2)ppm.

Preparation 69

1-[2-[2-(Diethylamino)ethoxy]-5-nitrophenyl]ethanone hydrobromide

Heat a mixture of 30.5 g (168 mmol) of 2-hydroxy-5-nitroacetophenone, 52.2 g (378 mmol) of potassium carbonate, 12.5 g (83 mmol) of potassium iodide, 36.2 g (210 mmol) of 2-diethylaminoethyl chloride hydrochloride, and 300 mL of acetone at reflux with stirring. Monitor the progress of the reaction by thin-layer chromatography on silica gel (methylenechloride/methanol; 95+5). When the reaction is complete, remove the solvent in vacuo. Dissolve the residue in water and extract four times with diethyl ether. Wash the organic phase with water, diluted sodium hydroxide, water and saturated sodium chloride solution. Dry the ethereal solution over anhydrous sodium sulfate, filter the drying agent and remove the solvent in vacuo. Dissolve the resulting oil in ethanol and add hydrobromic acid. Remove the solvent in vacuo and recrystallize the residue from ethanol to provide the title compound.

NMR (DMSO-d$_6$): δ=1.26(t,6), 2.65(s,3), 3.26–3.30 (m,4), 3.67(q,2), 4.65(t,2), 7.46(d,1), 8.41–8.48(m,2) and 9.64(br s,1)ppm.

Preparation 70

1-[5-Amino-2-[2-(diethylamino)ethoxy]phenyl]ethanone hydrobromide

To 5.0 9 g (17.8 mmol) of 1-[2-[2-(diethylamino)ethoxy]-5-nitrophenyl]ethanone in 50 mL of ethanol add 20.1 g (89.2 mmol) of tin(II) chloride dihydrate and heat the mixture to reflux with stirring for two hours. After cooling remove the solvent in vacuo. Add water and adjust the pH to 12 with potassium hydroxide. Add ethyl acetate and filter the mixture through celite. Separate the layers of the filtrate and extract the aqueous layer twice with ethyl acetate. Wash the combined organic layers with water, saturated sodium chloride solution, and dry over anhydrous sodium sulfate. Remove the solvent in vacuo and dissolve the remainder in ethanol. Add hydrobromic acid and remove the solvent in vacuo. Recrystallize the remaining solid from ethanol to produce the title compound.

NMR (DMSO-d$_6$): δ=1.28(t,6), 2.63(s,3), 3.08(q,4), 3.67(m,2), 4.58(t,2), 7.41(d,1), 7.62(dd,1), 7.67(d,1) and 9.80(br s,3)ppm.

Preparation 71

1-[2-[2-(Diethylamino)ethoxy]-5-nitrophenyl]-3-phenyl-2-propen-1-one hydrobromide To 3.70 g (13.2 mmol) of 1-[2-[2-(diethylamino)ethoxy]-5-nitrophenyl]ethanone in 50 mL of methanol add 1.40 g (13.2 mmol) of benzaldehyde. To this solution add dropwise a solution of 0.20 g (3.6 mmol) of potassium hydroxide in 6 mL of water. Stir the mixture for 24 hours and then add 50 mL of water. Collect the precipitate and dissolve it in ethanol. Add hydrobromic acid and remove the solvent in vacuo. Recrystallize the remaining solid from ethanol to yield the title compound.

NMR (DMSO-d$_6$): δ=1.08(t,6), 3.10–3.16(m,4), 3.53–3.54(m,2), 4.61(t,2), 7.42–7.49(m,5), 7.59(d,1), 7.83(dd,2), 8.32(d,1), 8.46–8.50(dd,1) and 9.43(br s,1) ppm.

Preparation 72

1-[5-Amino-2-[2-(diethylamino)ethoxy]phenyl]-3-phenylpropan-1-one

To 5.0 g (13.6 mmol) of 1-[2-[2-(diethylamino)ethoxy]-5-nitrophenyl]-3-phenyl-2-propen-1-one in 250 mL of ethanol add 0.5 g of palladium on carbon (10%). Hydrogenate the mixture at 22 psi until the theoretical amount of hydrogen has been absorbed. Filter the reaction and remove the solvent in vacuo to provide the title compound.

NMR (CDCl$_3$): δ=0.98(t,6), 2.54(q,4), 2.79(t,2), 3.00(t,2), 3.36(t,2), 3.52(br s,2), 4.02(t,2), 6.76–6.82 (m,2), 7.04(d,1) and 7.20–7.32(m,5)ppm.

Preparation 73

1-[5-Amino-2[2-(diethylamino)ethoxy]phenyl]3-phenyl-2-propen-1-one

To 5.00 g (13.6 mmol) of 1-[2-[2-(diethylamino)ethoxy]-5-nitrophenyl]-3-phenyl-2-propen-1-one in 50 mL of ethanol add 9.20 g (40.8 mmol) of tin(II) chloride dihydrate and heat the mixture to reflux with stirring for two hours. After cooling remove the solvent in vacuo. Add water and adjust the pH to 12 with potassium hydroxide. Add ethyl acetate and filter the mixture through celite. Separate the layers of the filtrate and extract the aqueous layer twice with ethyl acetate. Wash the combined organic layers with water, saturated sodium chloride solution, and dry over anhydrous sodium sulfate. Remove the solvent in vacuD to provide the title compound.

NMR (CDCl$_3$): δ=0.96(t,6). 2.56(q,4), 2.82(t,2), 4.08(t,2), 6.78–6.92(m,2), 7.04(d,1) and 7.38–7.70(m,7) ppm.

EXAMPLES

Example 1

N-[4-[[2-(Diethylamino)ethyl]amino]phenyl]methanesulfonamide

To tetrahydrofuran (15 mL) under a nitrogen atmosphere add 2.0 g (6.8 mmol) of 2-diethylamino-N-[4-[(methylsulfonyl)amino]phenyl]acetamide and 0.60 g (16 mmol) of lithium aluminum hydride. When the addition is complete stir the reaction at reflux. Monitor the progress of the reaction by thin-layer chromatography on silica gel ($CH_2Cl_2$:MeOH, 9:1). Upon completion of the reaction add 1 mL of $H_2O$, 1 mL of 2N NaOH, 2 mL of water, and 50 mL ethyl acetate. The solid material is removed by suction filtration through celite and the solvent is removed in vacuo. Chromatrograph the resulting oil on silica gel with $CH_2Cl_2$:MeOH, 9:1 followed by $CH_2Cl_2$ MeOH, 2:1. Combine the product fractions and remove the solvent in vacuo. Dissolve the residue in 48% aqueous HBr and remove the solvent. Recrystallize from methanol/isopropanol to afford the title compound.

NMR (DMSO-$d_6$): (300 MHz) δ=1.20(t,6), 2.84(s,3), 3.2(br s,6), 3.34(br, 4), 6.64(d,2), 7.04(d,2), 9.08(s,1)ppm.

Example 2

N-[4-[(2-Diethylamino)ethyl(phenylmethyl)amino]phenyl]methanesulfonamide E-butenedioic acid salt (1:1)

To 20 mL of tetrahydrofuran under nitrogen add 0.80 g (21 mmol) of lithium aluminum hydride and 5.20 g (13.4 mmol) of 2-(diethylamino)-N-[4-[(methylsulfonyl)amino]phenyl]-N-(phenylmethyl)acetamide. When the addition is complete, stir the reaction mixture at reflux. Monitor the reaction by thin-layer chromatography on silica gel (methylene chloride:methanol, 9:1). Upon completion of the reaction, add 1 mL of water, 1 mL of 2N sodium hydroxide, then 3 mL of water. Remove the precipitate by suction filtration and wash with ethyl acetate. Evaporate the combined filtrates in vacuo. Dissolve resulting oil in methanol and add 0.96 g (8.3 mmol) of fumaric acid. Evaporate solvent and recrystallize the resulting solid from methanol to afford the title compound.

NMR (DMSO-$d_6$): δ=1.01(t,6), 2.60–2.80(m,6), 2.83(s,3), 3.56(br t,2), 4.55(s,2), 3.0–5.5(br,2), 6.56(s,2), 6.67(d,2), 7.00(d,2), 7.20–7.40(m,5) and 9.05(s,1)ppm.

Example 3

N-[4-[[2-(Diethylamino)-3-(2-methylpropoxy)propyl](phenylmethyl)amino]phenyl]methanesulfonamide phosphoric acid salt (1:1)

To 10 mL of tetrahydrofuran under a nitrogen atmosphere add 3.1 g (6.5 mmol) of N-[2-diethylamino-3-(2-methylpropoxy)]propyl-N-[4-[(methylsulfonyl)amino]phenyl]benzamide and 0.71 g (19 mmol) of lithium aluminum hydride. When the additions are complete allow the reaction to stir at reflux. Monitor the progress of the reaction by thin-layer chromatography ($CH_2CL_2$:MeOH, 9:1). Upon completion of the reaction remove the heat and add 6 mL of $H_2O$, mL of 2N NaOH, 3 mL of $H_2O$ and 50 mL EtOAc. Remove the precipitate by suction filtration and remove the solvent in vacuo. Chromatograph the oil on silica gel $CH_2Cl_2$:MeOH, 24:1. Dissolve the oil in MeOH and acidify with 85% $H_3PO_4$. Remove the solvent in vacuo. Recrystallize the solid in acetonitrile to provide the title compound.

NMR (DMSO-$d_6$): δ=0.88(d,6), 0.95(t,6), 1.80(m,1), 2.5–2.8(m,4), 2.82(s,3), 3.14(d,2), 3.16(m,1), 3.3–3.7(m,4), 4.57(d,1), 4.69(d,1), 6.66(d,2), 6.97(d,2), 7.2(m,3), 7.3(m,2), 8.5–8.11(br,3), 9.01(br s,1)ppm.

Example 4

N-[4-(Piperazin-1-yl)phenyl]methanesulfonamide hydrochloride

Hydrogenolyze a suspension of 7.03 g (18.2 mmol) of N-[4-[4-(phenylmethyl)piperazin-1-yl]phenyl]methanesulfonamide in 400 mL of 50% aqueous ethanol over 0.35 g of 10% palladium on activated carbon catalyst at 50 psi. At the completion of the reaction remove the catalyst by filtration and evaporate the solvent in vacuo. Recrystallize the residue from ethanol to obtain the title compound.

NMR ($D_2O$): δ=3.08(s,3), 3.48(m,8), 7.16(d,2) and 7.31(d,2)ppm.

Example 5

N-[4-[4-(Phenylmethyl)piperazin-1-yl]phenyl]methanesulfonamide 1.2 hydrochloride To a chilled solution of 9150 g (35.5 mmol) of 4-[4-(phenylmethyl-1-piperazinyl]benzenamine in 100 mL of acetonitrile, add 6.49 g (37 mmol) of methanesulfonic anhydride in 50 mL of acetonitrile. Allow the reation mixture to stir at room temperature for 5 h. After this time, filter the resulting precipitate, add 100 mL of saturated aqueous sodium bicarbonate solution and extract this solution with 2×100 mL of methylene chloride. Wash the combined methylene chloride layers with 100 mL of saturated aqueous sodium chloride solution. Remove the solvent in vacuo. Dissolve the residue in 100 mL of methanol and acidify the solution with hydrogen chloride gas to pH=1. The solution is cooled and the resulting solid filtered to obtain the title compound.

NMR (DMSO-$d_6$): δ=2.87(s,3), 3.03–3.25(m,4), 3.33(d,2), 3.63–3.81(m,2), 4.37(d,2), 6.96(d,2), 7.12(d,2), 7.47(m,3), 7.66(m,2), 9.37(br s,1) and 11.38 (br s,1)ppm.

Example 6

N-[4-[4-Methylpiperazin-1-yl]phenyl]methanesulfonamide dihydrochloride

Dissolve 10.0 g (35.3 mmol) of 4-[4-methyl-1-piperazinyl]benzenamine 2.05 hydrochloride in 100 mL $H_2O$ and make basic (pH=14) with 2N sodium hydroxide solution. Extract the aqueous solution with 3×150 mL of methylene chloride. Remove the solvent in vacuo. Dissolve the residue in 150 mL of acetonitrile and add 6.76 g (39 mmol) of methanesulfonic anhydride to the solution. Heat the reaction mixture to 50° C. for 2 h. After this time, add 10 mL of water and concentrate to 50 mL volume. Add 200 mL water and neutralize (pH=8) the aqueous mixture with saturated sodium bicarbonate solution. Extract the neutral solution with 3×200 mL of methylene chloride. Remove the solvent in vacuo. Dissolve the residue in 250 mL of methanol and bubble hydrogen chloride gas through the solution until pH=1. Store the mixture at −20° C. overnight and collect the resulting solid by filtration to obtain the title compound.

NMR (D₂O): δ=2.97(s,3), 3.06(s,3), 3.11–3.39(m,4), 3.68(d,2), 3.85(d,2), 7.16(d,2) and 7.29(d,2)ppm.

Example 7

N-[4-[4-Ethyl-3-[(2-methylpropoxy)methyl]piperazin-1-yl]phenyl]methanesulfonamide, dihydrochloride To 5 mL of tetrahydrofuran under a nitrogen atmosphere add 2.6 g (6.8 mmol) of N-[4-[4-ethyl-5-[(2-methylpropoxy)methyl]-2-oxopiperazin-1-yl]phenyl]-methanesulfonamide hydrochloride and 0.51 (13 mmol) of lithium aluminum hydride. When the additions are complete stir the reaction at reflux. Monitor the progress of the reaction by thin-layer chromatography on silica gel (CH₂Cl₂:MeOH, 9:1). Upon completion of the reaction cool to room temperature and add 0.5 mL of H₂O, 0.5 mL of 2N NaOH, 1.5 mL of H₂O, and 50 mL of EtOAc. Remove the precipitate by suction filtration through celite and remove the solvent in vacuo. Chromatograph the residue on silica gel with CH₂Cl₂:MeOH. Combine the product fractions and remove the solvent in vacuo. Dissolve the residue in methanolic HCl and remove the solvent in vacuo. Recrystallize the material from isopropanol to afford the title compound.

NMR (DMSO-d₆): (300 MHz)δ=0.99(d,6), 1.28 and 1.33(t,3 total), 1.85(m,1), 2.88 and 2.88(s,3 total), 3.0–4.0(m,13), 6.96 and 7.00(d,2 total), 7.14(d,2), 9.40(br s,1), 10.9(br,1), and 11.3(br,1)ppm.

Example 8

N-[4-[4-[2-(Cyclopentyl)ethyl]hexahydro-1H-1,4-diazepin-1-yl]phenyl]methanesulfonamide In a manner similar to Example 1 react N-[4-[4-(2-[cyclopentyl]ethyl]hexahydro-2-oxo-1H-1,4-diazepin-1-yl]phenyl]methanesulfonamide with lithium aluminum hydride to obtain the title compound.

Example 9

N-[3,5-Dimethyl-4-[[(1-(phenylmethyl)pyrrolidin-3-yl)methyl]amino]phenyl]methanesulfonamide In a manner similar to Preparation 14 react N-(2,6-dimethyl-4-nitrophenyl)-1-(phenylmethyl)-3-pyrrolidinemethanamine with tin(II) chloride dihydrate in ethanol, then with methanesulfonic anhydride in acetonitrile to obtain the title compound.

Example 10

N-[4-[[4-[[2-(Cyclohexyl)ethyl]amino]hexyl](phenylmethyl)amino]phenyl]methanesulfonamide In a manner similar to Example 1 react 4-[[2-(cyclohexyl)ethyl]amino]-N-[4-[(methylsulfonyl)amino]-phenyl]-N-(phenylmethyl)hexanamide with lithium aluminum hydride to obtain the title compound.

Example 11

N-[4-[[2-[Ethyl(5-methylhexyl)amino]ethyl](2-propenyl)amino]phenyl]methanesulfonamide In a manner similar to Example 5 react N-(4-aminophenyl)-N'-ethyl-N'-(5-methylhexyl)-N-(2-propenyl)-1,2-ethanediamine with methanesulfonic anhydride in acetonitrile to obtain the title compound.

Example 12

N-[4-[Ethyl([[2-[[octyl(phenylmethyl)amino]methyl]-cyclopropyl]methyl])amino]phenyl]methanesulfonamide In a manner similar to Example 1 react N-ethyl-N-[4-[(methylsulfonyl)amino]phenyl]-N'-octyl-N'-(phenylmethyl)cyclopropane-1,2-dicarboxamide with lithium aluminum hydride to obtain the title compound.

Example 13

N-[4-[Ethyl[4-[phenylmethyl)(2-propenyl)amino]cyclohexylmethyl]amino]phenyl]methanesulfonamide In a manner similar to Preparation 7 react N-[4-[ethyl[(4-oxocyclohexyl)methyl]amino]phenyl]methanesulfonamide with 2-propenylbenzenemethanamine and sodium cyanoborohydride in methanol to obtain the title compound.

Example 14

N-[4-[2-(Diethylamino)ethoxy]phenyl]methanesulfonamide methanesulfonic acid salt To a solution of 2.8 g (12.4 mmol) of 4-[2-(diethylamino)ethoxy]benzenamine dissolved in 30 mL of acetonitrile cooled to 0° C. add 2.6 g (15 mmol) of methanesulfonic anhydride. Stir the reaction mixture for 4 h at ambient temperature. Remove the solvent in vacuo and recrystallize the residue from acetonitrile/ethyl acetate to obtain the title compound.

NMR (D₂O): δ=1.33(t,6), 2.80(s,3), 3.07(s,3), 3.33(quar,4), 3.61(t,2), 4.40(t,2), 7.06(d,2) and 7.29(d,2)ppm.

Example 15

N-[4-[[2-(Diethylamino)ethyl]thio]phenyl]methanesulfonamide hydrochloride

To a solution of 4.5 g (20 mmol) of 4-[[2-(diethylamino)ethyl]thio]benzenamine in 100 mL of acetonitrile add 3.84 g (22 mmol) of methanesulfonic anhydride. Heat the reaction mixture at 50° C. for ca. 5 h. After this time, add 250 mL of water and make the aqueous mixture basic (pH=14) with 4N sodium hydroxide solution. Wash the basic solution with 150 mL of methylene chloride. Make the aqueous solution acidic (pH=1) with 6N hydrochloric acid solution. Extract the acidic solution with 150 mL of diethyl ether. Make the aqueous solution basic (pH=8) with saturated aqueous sodium bicarbonate solution and extract with 2×150 mL of methylene chloride. Remove the solvent in vacuo and chromatograph the residue on silica gel eluting with a gradient mixture of methylene chloride/methanol (methanol 1%–10%). Combine the fractions containing the product and remove the solvent in vacuo. Dissolve the residue in 75 mL of 2-propanol and bubble hydrogen chloride gas through the solution until pH=1. Precipitate the product by addition of diethyl ether to obtain the title compound.

NMR (DMSO-d₆): δ=1.16(t,6), 3.00(s,3), 3.12(m,6), 3.32(m,2), 7.21(d,2), 7.45(d,2) and 9.88(br s,1)ppm.

Example 16

N-[4-[3-(Diethylamino)propoxy]phenyl]methanesulfonamide

To a solution of 6.00 g (20.3 mmol) of 4-[3-(diethylamino)propoxy)benzenamine dihydrochloride in 50 mL of pyridine under a nitrogen atmosphere and cooled to ca −10° C. add 2.0 mL (25.4 mmol) of methanesulfonyl chloride dropwise. Maintain the temperature below 0° C. during the addition. Stir the reaction mixture at ambient temperature for 5 h then add 10 mL of H$_2$O. Evaporate the solvent in vacuo and dissolve the residue in 50 mL of H$_2$O (pH=ca. 3). Extract the aqueous solution with 2×100 mL of diethyl ether. Adjust the pH of the aqueous solution to pH=13 with 20% aqueous sodium hydroxide solution and extract this solution with 3×50 mL of methylene chloride. Adjust the pH of the aqueous solution to pH=8.5 with concentrated hydrochloric acid and saturate the solution with sodium chloride. Extract the mixture with 3×100 mL of methylene chloride. Wash the organic extracts with 25 mL of saturated aqueous sodium chloride solution, combine the extracts and dry over anhydrous sodium sulfate. Remove the drying agent by filtration and evaporate the solvent in vacuo to obtain the title compound.

NMR (CDCl$_3$): δ=1.20(t,6), 2.12(m,2), 2.83(quar,4), 2.89(m,2), 2.95(s,3), 4.01(t,2), 6.85(d,2) and 7.23(d,2) ppm.

Example 17 trans-N-[4-[2-(Diethylamino)cyclohexyloxy]phenyl]-methanesulfonamide methanesulfonic acid salt To 3.16 g (12 mmol) of trans-2-(4-aminophenoxy)-N,N-diethylcyclohexanamine in 20 mL of acetonitrile under an N$_2$ atmosphere add 2.10 g (10 mmol) of methanesulfonic acid anhydride. Stir the reaction for 3 h at 50° C. Cool the reaction mixture and remove the solvent in vacuo. Recrystallize the resulting product from acetone/ether to afford the title compound.

NMR (DMSO-d$_6$) (300 MHz) δ=1.22-1.29(m,6), 1.31-1.78 (m,6), 2.05-2.14(m,2), 2.31(s,3), 2.92(s,3), 3.05-3.12(m,2), 3.19-3.25(m,2), 3.53-3.62(m,1), 4.60-4.65(,1), 7.06(d,2) and 7.19(d,2)ppm.

Example 18

N-[4-[1-(Butylpiperidin-4-yl)oxy]-2-methylphenyl]methanesulfonamide methanesulfonic acid salt In a manner similar to Example 17 react 4-[4-amino-3-methylphenoxy]-1-butylpiperidine with methanesulfonic acid anhydride in acetonitrile to obtain the title compound.

Example 19

N-[4-[[3-(4-Methyl-1-piperidinyl)propyl]thio]phenyl]-methanesulfonamide hydrochloride Dissolve 9.50 g (36 mmol) of 1-[3-[[4-aminophenyl]-thio]propyl]-4-methylpiperidine in 200 mL of acetonitrile. Add 6.5 g (38 mmol) of methanesulfonic anhydride and heat the mixture to 50° C. for 5 h. After 5 h, quench with 5 mL of water and concentrate solvent in vacuo to a 50 mL volume. Dissolve in 200 mL of water and 200 mL of methylene chloride and then make basic (pH=14) with 2N sodium hydroxide. Separate the layers and extract the organic layer with 3×100 mL of water. Neutralize (pH=8) the combined aqueous layers with 6N hydrochloric acid solution. Extract aqueous solution with 3×250 mL of methylene chloride. Combine the organic extracts and remove the solvent in vacuo. Purify this crude material using flash column chromatography with 250 g flash silica gel (Baker) and eluting with a methanol/methylene chloride gradient (0–5% methanol). Collect the fractions containing the product compound and remove the solvent in vacuo. Dissolve the residue in 100 mL of methanol and acidify to pH=1 with hydrochloric acid gas. Evaporate this solution and triturate with acetonitrile to provide the title compound.

NMR (DMSO): δ=0.90(d,2.6), 0.97(d,0.4), 1.47(m,2), 1.56(m,1), 1.73(m,2), 1.96(m,2), 2.83(m,2), 2.97(t,2), 2.99(s,3), 3.08(m,2), 3.34(m,2), 7.18(d,2), 7.37(d,2), 9.82(br s,1) and 10.2(br s,1)ppm.

Example 20

N-[4-[[3-(4-Methylpiperidin-1-yl)propyl]sulfinyl]-phenyl]methanesulfonamide hydrochloride Dissolve 4.48 g (11.83 mmol) of N-[4-[[3-(4-methyl-1-piperidinyl)propyl]thio]phenyl]methanesulfonamide hydrochloride in 70 mL of methanol and add 2.68 mL of 30% aqueous hydrogen peroxide and stir at room temperature for 24 h. After 24 h, quench reaction with 5% aqueous sodium sulfate until the solution gives a negative test with potassium iodide paper. Make basic (pH=8) with saturated sodium bicarbonate solutin. Add 100 mL of water and extract with 200 mL of methylene chloride. Remove the solvent of the organic layer in vacuo. Purify this residue by flash column chromatography using 150 g flash silica gel (Baker) and eluting with a methylene chloride/methanol gradient (0–10% CH$_3$OH). Combine the product fractions and remove the solvent in vacuo. Dissolve this residue in 25 mL of ethanol and acidify to pH=1 with hydrogen chloride. Add 25 mL of diethyl ether and collect the resulting solid by filtration to provide the title compound.

NMR (DMSO): δ=0.90(d,3), 1.38-1.65(m,3), 1.73 (m, 2), 1.94(m,1), 2.06(m,1), 2.84(m,3), 3.07(m,3), 3.09(s,3), 3.36(m,2), 7.40(d,2), 7.65(d,2), 10.28(br s,1) and 10.50(br s,1)ppm.

Example 21

N-[4-[[3-(4-Methylpiperidin-1-yl)propyl]sulfonyl]-phenyl]methanesulfonamide hydrochloride Dissolve 1.90 g (5.3 mmol) of N-[4-[[3-(4-methyl-piperidin-1-yl)propyl]sulfinyl]phenyl]methanesulfonamide in 50 mL of methanol and add 2.29 g (10.6 mmol) of 3-chloroperoxybenzoic acid. Stir at room temperature for 24 h. Ater 24 h, quench reaction with 5% aqueous sodium sulfite until the solution gives a negative test with potassium iodide paper. Make basic (pH=8) with saturated sodium bicarbonate solution. Add 50 mL of water and extract with 3×100 mL of methylene chloride. Remove the solvent of the combined organic layer in vacuo. Purify this residue by flash column chromatography using 50 g of flash silica gel (Baker) and eluting with a methylene chloride/methanol gradient (0–10% CH$_3$OH). Combine the product fraction and remove the solvent in vacuo. Dissolve the residue in 20 mL of ethanol and 20 mL of diethyl ether. Acidify this solution with hydrogen chloride gas and collect the resulting solid by filtration to provide the title compound.

NMR (DMSO-d$_6$): δ=0.90(d,3), 1.32-1.82(m,5), 2.00(m,2), 2.72-2.96(m,3), 3.00-3.15(m,3), 3.17(s,3), 3.40(t,2), 7.42(d,2), 7.86(d,2) and 9.8-10.8(br, 2)ppm.

Example 22

N-[2-Methyl-4-[[3-[bis(1-methylethyl)amino]propyl]thio]phenyl]methanesulfonamide hydrochloride In a manner similar to Example 15 react 2-methyl-4-[[3-[bis-(1-methylethyl)amino]propyl]thio]benzenamine with methanesulfonic anhydride in acetonitrile to obtain the title compound.

Example 23

N-[2-Methyl-4-[[3-[bis(1-methylethyl)amino]propyl]sulfinyl]phenyl]methanesulfonamide hydrochloride React N-[2-methyl-4-[[3-[bis(1-methylethyl)amino]propyl]thio]phenyl]methanesulfonamide hydrochloride with 30% aqueous hydrogen peroxide in a manner similar to Example 8 to obtain the title compound.

Example 24

N-[2-Methyl-4-[[3-[bis(1-methylethyl)amino]propyl]sulfonylphenyl]methanesulfonamide hydrochloride React N-[2-methyl-4-[[3-[bis(1-methylethyl)amino]propyl]sulfinyl]phenyl]methanesulfonamide with 3-chloroperoxybenzoic acid to obtain the title compound.

Example 25

N-[4-[(1-Butyl-2-pyrrolidinyl)methoxy]phenyl]ethanesulfonamide

React 4-[(1-butyl-2-pyrrolidinyl)methoxy]benzeneamine with ethanesulfonyl chloride in pyridine in a manner similar to Example 16 to obtain the title compound.

Example 26

N-[4-[2-(Diethylamino)-3-(2-methylpropoxy)propoxy]phenyl]methanesulfonamide phosphoric acid salt (1:1)

To 50 mL of ethanol under nitrogen add 4.22 g (13.0 mmol) of N,N-diethyl-3-(2-methylpropoxy-1-(4-nitrophenyl)-2-propanamine and 14.4 (64 mmol) of stannous chloride dihydrate. When the additions are complete, allow the reaction to stir at reflux. Monitor the progress of the reaction by thin-layer chromatography (ethyl acetate:hexane, 1:1). Upon completion of the reaction, remove the heat source and add 2N NaOH until basic. Remove the precipitate by suction filtration through celite and wash with EtOAc. The organic layer is separated, washed with brine, and dried ($Na_2SO_4$). Remove drying agent by filtration and remove solvent in vacuo. To the resulting oil is added 50 mL of acetonitrile and 2.5 g (14 mmol) of methanesulfonic anhydride. When the additions are complete, allow the reaction to stir at reflux for three hours. Upon completion of the reaction, the solvent is removed in vacuo and the residue is dissolved in $CH_2Cl_2$ and stirred vigorously with saturated aqueous $NaHCO_3$. The organic layer is separated and dried over anhydrous $Na_2SO_4$. Remove drying agent by filtration and remove solvent in vacuo. Chromatography of the oil on silica gel ($CH_2Cl_2$ MeOH 19:1) gives the free base of the title compound. Dissolve the oil in MeOH and acidify with 85% $H_3PO_4$. Treat the solution with activated charcoal and remove the solvent to give the title compound as an amorphorus solid.

NMR (DMSO-$d_6$): $\delta = 0.84$(d,6), 1.03(t,6), 1.8(m,1), 2.79(m,4), 2.88(s,3), 3.17(d,2), 3.34(br s,1), 3.58(m,2), 4.06(m,2), 6.93(d,2), 7.14(d,2), 9.43(br s,1)ppm.

Example 27

N-[4-[2-(Diethylamino)ethoxy]-3,5-dimethylphenyl]methanesulfonamide methanesulfonic acid salt To 4.55 g (19.3 mmol) of 2-(4-amino-2,6-dimethylphenoxy)-N,N-diethylethanamine in 40 mL of acetonitrile add 3.40 g (19.5 mmol) of methanesulfonic anhydride. After the addition is complete, stir the reaction for 2 hours at 50° C. Remove the solvent in vacuo. Recrystallize the residue from acetone/ether to obtain the title compound.

NMR (DMSO-$d_6$): $\delta = 1.26$(t,6), 2.24(s,6), 2.32(s,3), 2.94(s,3), 3.27–3.35(m,4), 3.52(br s,2), 4.04(t,2), 6.90(s,2), 9.38(br s,1) and 9.51(s,1).

Example 28

N-[3-Benzoyl-4-[(2-diethylamino)ethoxy]phenyl]methanesulfonamide hydrobromide

Heat a mixture of 3.0 g (9.6 mmol) of [5-amino-2-[2-diethylamino)ethoxy]phenyl](phenyl)methanone, 1.70 g (9.8 mmol) of methanesulfonic anhydride, and 60 mL of acetonitrile to reflux for six h. After cooling remove the solvent in vacuo. Distribute the residue between diethyl ether and sodium bicarbonate solution. Wash the ether layer with water and dry over anhydrous sodium sulfate. Remove the solvent in vacuo and purify the crude product by column chromatography on silica gel (methylene chloride:methanol 95:5). Dissolve the product in ethanol and add hydrobromic acid. Evaporate the solvent and recrystallize the solid to yield the title compound.

NMR (DMSO-$d_6$): $\delta = 1.00$(t,6), 2.92–2.96(m,4), 2.98(s,3), 3.22(m,2), 4.34(t,2), 7.21–7.78(m,8), 9.35(br s,1) and 9.69(s,1)ppm.

Example 29

4-[2-(Diethylamino)ethoxy]-3-acetylphenyl]methanesulfonamide methanesulfonic acid salt To 3.44 g (13.7 mmol) of 1-[5-amino-2-[2-(diethylamino)ethoxy]phenyl]ethanone in 50 mL of acetonitrile add 2.39 g (13.7 mmol) of methanesulfonic anhydride. Heat the mixture to reflux with stirring. After two h cool the reaction and remove the solvent in vacuo. Recrystallize the remaining solid from ethanol to yield the title compound.

NMR (DMSO-$d_6$): $\delta = 1.24$(t,6), 2.33(s,3), 2.57(s,3), 2.93(s,3), 3.23–3.28(m,4), 3.60(m,2), 4.43(t,2), 7.22(d,1), 7.41(dd,1), 7.46(d,1), 9.32(br s,1) and 9.64(s,1)ppm.

Example 30

N-[4-[2-(Diethylamino)ethoxy]-3-(1-oxo-3-henylpropyl)phenyl]methanesulfonamide hydrobromide To 4.30 g (13.8 mmol) of 1-[5-amino-2-[2-(diethylamino)ethoxy]phenyl]-3-phenylpropan-1-one in 50 mL of acetonitrile add 2.49 g (14.3 mmol) of methanesulfonic anhydride. Heat the mixture to reflux with stirring for two h. After cooling remove the solvent in vacuo. Partition the remainder between diethylether and sodium bicarbonate solution. Wash the ether layer with water and dry over anhydrous sodium sulfate. Remove the solvent in vacuo and purify the crude product by column chromatography on silica gel (methylene chloride:methanol 95:5) Dissolve the product in ethanol and add hydrobromic acid. Remove the solvent in vacuo and recrystallize the remaining solid to yield the title compound.

NMR (DMSO-$d_6$): $\delta = 1.14$(t,6), 2.91(m,2), 2.92(s,3), 3.16–3.18(br m,4), 3.29–3.34(m,2), 3.50(br s,2), 4.40(m,2), 7.18–7.39(m,6), 7.41–7.44(m,2), 9.30(br s,1) and 9.62(s,1)ppm.

Example 31

N-[4-[2-(Diethylamino)ethoxy]-3-(1-oxo-3-phenylpropenyl)phenyl]methanesulfonamide hydrobromide To 4.60 g (13.6 mmol) of 1-[5-amino-2[2-(diethylamino)ethoxy]phenyl]-3-phenylpropen-1-one in 50 mL of acetonitrile add 2.37 g (13.6 mmol) of methanesulfonic acid anhydride. Heat the mixture to reflux for two h with stirring. After cooling remove the solvent in vacuo. Partition the remaining compound between diethyl ether and sodium bicarbonate solution. Wash the ether layer with water and dry over anhydrous sodium sulfate. Remove the solvent in vacuo and purify the crude product by column chromatography on silica gel (methylene chloride:methanol 95:5). Dissolve the product in ethanol and add hydrobromic acid. Remove the solvent and recrystallize the remaining solid to yield the title compound.

NMR (DMSO-$d_6$): $\delta$=1.07(t,6), 2.96(s,3), 3.10–3.12 (m,4), 3.46–3.47(m,2), 4.42(t,2), 7.27(dd,1), 7.35(dd,1), 7.40–7.58(m,6), 7.75–7.79(m,2), 9.30(br s,1) and 9.66 (s,1)ppm.

We claim:

1. A compound of the following Formula I:

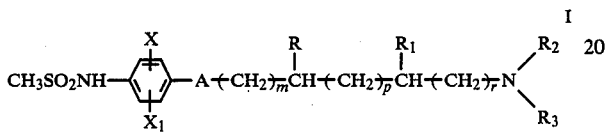

wherein:

$X$, $X_1$ are the same or independently hydrogen, lower alkyl or one of X and $X_1$ is hydrogen and the other is in the ortho position to A and is the group

A is O, S, SO, SO$_2$ or

R is hydrogen, methyl, ethyl or collectively with $R_1$ is a bond or an alkylene chain to form a saturated carbocyclic ring of from 3 to 6 ring atoms, or collectively with $R_2$ is a bond or alkylene chain to form a saturated monoheterocyclic ring of 5 to 6 ring atoms;

$R_1$ is hydrogen, methyl, ethyl or lower alkoxyloweralkyl;

$R_2$ is a $C_1$–$C_8$ straight or branched chain alkyl, allyl, optionally substituted phenyl loweralkyl, said phenyl group being substituted by 1–3 substituents selected from hydrogen, chlorine, bromine, loweralkoxy, loweralkyl and trifluoromethyl, cycloalkyl, cycloalkylloweralkyl, or together with $R_3$ is an alkylene chain to form a heterocyclic ring of from 4 to 7 ring atoms or together with $R_3$ forms the system —CH$_2$CH$_2$—O—CH$_2$CH$_2$— or

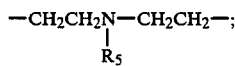

$R_3$ is hydrogen, $C_1$–$C_8$ straight or branched chain alkyl, allyl, optionally substituted phenyl loweralkyl, cycloalkyl, cycloalkylloweralkyl, said phenyl group being substituted by 1–3 substituents selected from hydrogen, chlorine, bromine, loweralkoxy, loweralkyl and trifluoromethyl;

$R_4$ is hydrogen $C_1$–$C_8$ straight or branched chain alkyl, allyl, optionally substituted phenyl loweralkyl, cycloalkylloweralkyl, said phenyl group being substituted by 1–3 substituents selected from hydrogen, chlorine, bromine, loweralkoxy, loweralkyl and trifluoromethyl or together with $R_2$ is an alkylene chain to form a saturated diheterocyclic ring of from 6 to 7 ring atoms;

$R_5$ is hydrogen, $C_1$–$C_8$ straight or branched chain alkyl;

B is lower alkyl, phenyl, —CH=CH—D, or —CH$_2$—CH$_2$—D;

D is

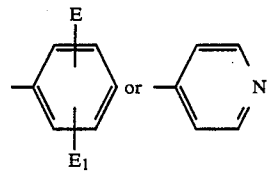

where E,$E_1$, are the same or independently hydrogen, lower alkyl, lower alkoxy or halogen;

m,p and r are the integers 0,1 or 2;

and the pharmaceutically acceptable salts thereof;

with the provisos that:

(a) when R and $R_1$ form a ring then $R_2$ together with $R_4$ cannot be a ring, (b) the sum of m,p and r cannot be greater than 3, (c) when one of X or $X_1$ is the group

then A must be —O—, (d) when A is —O—, —S—, or

and either or both of $R_2$ and $R_3$ are optionally substituted phenyl loweralkyl then the linkage between —A— and

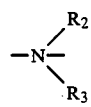

cannot consist of a straight or branched chain alkyl.

2. A compound of claim 1 wherein A is —O—.

3. A compound of claim 1 wherein A is —S—.

4. A compound of claim 1 wherein A is —SO—.

5. A compound of claim 1 wherein A is —SO$_2$—.

6. A compound of claim 1 wherein A is —N—.

7. A compound of claim 2 which is N-[4-[2-(diethylamino)ethoxy]phenyl]methanesulfonamide.

8. A compound of claim 2 which is N-[4-[3-(diethylamino)propoxy]phenyl]methanesulfonamide.

9. A compound of claim 2 which is N-[4-[2-(diethylamino)cyclohexyloxy]phenyl]methanesulfonamide.

10. A compound of claim 2 which is N-[4-[2-(diethylamino)ethoxy]-3,5-dimethylphenyl]methanesulfonamide.

11. A compound of claim 2 which is N-[4-[(2-diethylamino)ethoxy]-3-acetylphenyl]methanesulfonamide.

12. A compound of claim 2 which is N-[3-benzoyl-4-[(2-diethylamino)ethoxy]phenyl]methanesulfonamide.

13. A compound of claim 2 which is N-[4-[(2-diethylamino)ethoxy]-3-(1-oxo-3-phenylpropyl)phenyl]methanesulfonamide.

14. A compound of claim 2 which is N-[4-[(2-diethylamino)ethoxy]-3-(1-oxo-3-phenyl-2-propenyl)phenyl]methanesulfonamide.

15. A compound of claim 3 which is N-[4-[[2-(diethylamino)ethyl]thio]phenyl]methanesulfonamide.

16. A compound of claim 3 which is N-[4-[[3-(4-methyl-1-piperidinyl)propyl]thio]phenyl]methanesulfonamide.

17. A compound of claim 4 which is N-[[4-[3-(4-methylpiperidin-1-yl)propyl]sulfinyl]phenyl]methanesulfonamide.

18. A compound of claim 5 which is N-[4-[[3-(4-methylpiperidin-1-yl)propyl]sulfonyl]phenyl]methanesulfonamide.

19. A compound of claim 6 which is N-[4-[(2-(diethylamino)ethyl)amino]phenyl]methanesulfonamide.

20. A compound of claim 6 which is N-[4-[2-(diethylamino)ethyl(phenylmethyl)amino]phenyl]methanesulfonamide.

21. A compound of claim 6 which is N-[4-[(2-diethylamino)-3-(2-methylpropoxy)propyl)](phenylmethyl)amino]phenyl]methanesulfonamide.

22. A compound of claim 6 which is N-[4-(piperazin-1-yl)phenyl]methanesulfonamide.

23. A compound of claim 6 which is N-[4-[4-(phenylmethyl)piperazin-1-yl]phenyl]methanesulfonamide.

24. A compound of claim 6 which is N-[4-[4-methylpiperazin-1-yl]phenyl]methanesulfonamide.

25. A compound of claim 6 which is N-[4-[4-ethyl-3-[(2-methylpropoxy)methyl]piperazin-1-yl]phenyl]methanesulfonamide.

26. A pharmaceutical composition comprising a therapeutically effective amount of a compound of claim 1 together with a non-toxic pharmaceutically acceptable carrier.

* * * * *

UNITED STATES PATENT AND TRADEMARK OFFICE
CERTIFICATE OF CORRECTION

PATENT NO. : 4,906,634

DATED : March 6, 1990

INVENTOR(S) : S. Greenberg, et al.

It is certified that error appears in the above-identified patent and that said Letters Patent is hereby corrected as shown below:

Column 1, line 18
    "III agents are 15 effective" should read
    ---- III agents are effective ----.

Column 1, lines 56 & 57
    "-$CH_2$-CH-O-$CH_2CH_2$-" should read
    ---- $CH_2CH_2$-O-$CH_2$-$CH_2$- ----.

Column 1, line 63
    "$R_3$ $C_1$-$C_8$" should read
    ---- $R_3$ is hydrogen, $C_1$-$C_8$ ----.

Column 8, lines 17 & 18
    "wherein A is" should read
    ---- wherein A is -N-. ----
                           |
                           $R_4$ Column 8, line 28
    "HN-ALK-$NR_2R_1$" should read
     |
    $R_4$
    ---- HN-ALK-$NR_2R_3$ ----.
         |
       $R_4$

UNITED STATES PATENT AND TRADEMARK OFFICE
CERTIFICATE OF CORRECTION

PATENT NO. : 4,906,634
DATED : March 6, 1990
INVENTOR(S) : S. Greenberg, et al.

It is certified that error appears in the above-identified patent and that said Letters Patent is hereby corrected as shown below:

Column 8, line 63
"N,N-dimethylforamide" should read
---- N,N-dimethylformamide ----.

Column 9, line 38
"Note: $R_3 \neq H$"
       bz = benzyl   should read
----Note: n = 1-3
       $R_3 \neq H$
       bz = benzyl. ----

Column 14, line 17
"NMR (CDCl3)" should read
---- NMR ($CDCl_3$) ----.

Column 14, line 22
"4-L4-Phenylmethyl" should read
---- 4-[4-Phenylmethyl ----.

Column 14, line 25
"tin (II)" should read
---- tin (II) ----.

Column 15, line 15
"736 (d,2) ppm" should read
---- 7.36 (d,2) ppm ----.

UNITED STATES PATENT AND TRADEMARK OFFICE
CERTIFICATE OF CORRECTION

PATENT NO. : 4,906,634
DATED : March 6, 1990
INVENTOR(S) : S. Greenberg, et al.

It is certified that error appears in the above-identified patent and that said Letters Patent is hereby corrected as shown below:

Column 15, line 18
"N-L-4-[(phenylmethyl" should read
---- N-[4-[(phenylmethyl ----.

Column 15, line 32
"2 X 100 mL acetate" should read
---- 2 X 100 mL of ethyl acetate ----.

Column 15, line 38
"7,2-7.4" should read
---- 7.2-7.4 ----.

Column 15, line 42
"2-Chloro-[4-](" should read
---- 2-Chloro-N-[4-[( ----.

Column 16, line 6,7&8
"99 (s,3)
NMR (DMSO-$d_6$) δ = 0.87(t,6), 2.59(q,4), 2.
3 20 (br s,2)," should read
----NMR (DMSO-$d_6$): δ = 0.87(t,6), 2.59(q,4),
2.99(s,3), 3.20(br s,2), ----.

Column 16, line 41
"$NaSO_4$," should read
---- $Na_2SO_4$ ----.

UNITED STATES PATENT AND TRADEMARK OFFICE
CERTIFICATE OF CORRECTION

PATENT NO. : 4,906,634
DATED : March 6, 1990
INVENTOR(S) : S. Greenberg, et al.

It is certified that error appears in the above-identified patent and that said Letters Patent is hereby corrected as shown below:

Column 16, line 50
  "(2-methylpropoxy)-N1-(4-" should read
  --(2-methylpropoxy)-$N^1$-(4- --

Column 17, line 3
  "4-Ethyl-5-L (2-methyl" should read
  ---- 4-Ethyl-5-[(2-methyl ----.

Column 17, line 62
  "1-Diethyl-3(2-methyl" should read
  ---- N', N'-Diethyl-3-(2-methyl ----.

Column 19, line 24
  "(pH 11)" should read
  ---- (pH > 11) ----.

Column 19, line 35
  "4-fluoro1-" should read
  --- 4-fluoro-1- ----.

Column 19, line 41
  "hexahydro 1H-" should read
  ---- hexahydro-1H- ----.

Column 19, line 43
  "N-[2(cyclopentyl)" should read
  ---- N-[2-(cyclopentyl) ----.

UNITED STATES PATENT AND TRADEMARK OFFICE
CERTIFICATE OF CORRECTION

PATENT NO. : 4,906,634

DATED : March 6, 1990

INVENTOR(S) : S. Greenberg, et al.

It is certified that error appears in the above-identified patent and that said Letters Patent is hereby corrected as shown below:

Column 19, line 51
"react 4-[2(cyclopentyl)" should read
---- 4-[2-(cyclopentyl) ----.

Column 19, line 68
"3pyrrolidinemethanol" should read
---- 3-pyrrolidinemethanol ----.

Column 20, line 37
"N-[4-L(methyl" should read
---- N-[4-[(methyl ----.

Column 20, line 47
"2- (Cyclohexyl)" should read
---- 4-[[2- (Cyclohexyl)

Column 20, line 49
"react N-[4(meth-" should read
---- react N-[4-[(meth----.

Column 20, lines 65 & 66
"N-ethyl-methyl" should read
---- N-ethyl-5-methyl ----.

Column 21, lines 5 & 6
"N-ethylN-(5" should read
---- N-ethyl-N-(5 ----.

UNITED STATES PATENT AND TRADEMARK OFFICE
CERTIFICATE OF CORRECTION

PATENT NO. : 4,906,634
DATED : March 6, 1990
INVENTOR(S) : S. Greenberg, et al.

It is certified that error appears in the above-identified patent and that said Letters Patent is hereby corrected as shown below:

Column 21, line 23
"(2-propenyl)1,2-" should read
---- (2-propenyl)-1,2- ----.

Column 21, line 32
"in mL of" should read
---- in 100 mL of ----.

Column 21, line 56
"propane 1,2-" should read
---- propane-1,2- ----.

Column 22, line 41
"Extract th aqueous" should read
---- Extract the aqueous ----.

Column 22, line 68
"Remov the" should read
---- Remove the ----.

Column 25, line 46
"obtain the tile" should read
---- obtain the title ----.

UNITED STATES PATENT AND TRADEMARK OFFICE
CERTIFICATE OF CORRECTION

PATENT NO. : 4,906,634
DATED : March 6, 1990
INVENTOR(S) : S. Greenberg, et al.

It is certified that error appears in the above-identified patent and that said Letters Patent is hereby corrected as shown below:

Column 27, line 5
"add 20.09" should read
---- add 20.0 g ----.

Column 27, lines 20 & 21
"3 64(quar,2)" should read
---- 3.64(quar,2) ----.

Column 28, line 20
"the progess" should read
---- the progress ----.

Column 28, line 33
"NMR (DMSO-d)" should read
---- NMR (DMSO-$d_6$) ----.

Column 28, line 50
"emove the solvent" should read
---- remove the solvent ----.

Column 29, line 12
"ethoxy]phenyl]phenyl]" should read
---- ethoxy]phenyl]phenyl ----.

Column 29, line 59
"To 5.0 9 g" should read
---- To 5.0 g ----.

UNITED STATES PATENT AND TRADEMARK OFFICE
CERTIFICATE OF CORRECTION

PATENT NO. : 4,906,634
DATED : March 6, 1990
INVENTOR(S) : S. Greenberg, et al.

It is certified that error appears in the above-identified patent and that said Letters Patent is hereby corrected as shown below:

Column 30, line 64
"solvent in vacuD" should read
---- solvent in vacuo ----.

Column 31, line 19
"by $CH_2Cl_2$ MeOH," should read
---- by $CH_2Cl_2$:MeOH, ----.

Column 31, line 63
"$H_2O$, mL of 2N" should read
---- $H_2O$, 1 mL of 2N ----.

Column 36, line 19
"bicarbonate solutin" should read
---- bicarbonate solution ----.

Column 38, line 41
"(1-oxo-3-henyl-" should read
----(1-oxo-3-phenyl- ----.

UNITED STATES PATENT AND TRADEMARK OFFICE
CERTIFICATE OF CORRECTION

PATENT NO. : 4,906,634

DATED : March 6, 1990

INVENTOR(S) : S. Greenberg, et al.

It is certified that error appears in the above-identified patent and that said Letters Patent is hereby corrected as shown below:

Claim 6, line 58

"A is -N-." should read $$\text{---- A is -N-. ----.}$$
$$|$$
$$R_4$$

Signed and Sealed this

Twenty-third Day of June, 1992

Attest:

DOUGLAS B. COMER

*Attesting Officer*     Acting Commissioner of Patents and Trademarks